United States Patent
Velan et al.

(10) Patent No.: US 9,996,216 B2
(45) Date of Patent: Jun. 12, 2018

(54) SMART DISPLAY DATA CAPTURING PLATFORM FOR RECORD SYSTEMS

(71) Applicant: medCPU Ltd., New York, NY (US)

(72) Inventors: Noam Velan, Tel Aviv (IL); Eyal Ephrat, New York, NY (US)

(73) Assignee: medCPU, Ltd., New York, NY (US)

( * ) Notice: Subject to any disclaimer, the term of this patent is extended or adjusted under 35 U.S.C. 154(b) by 61 days.

(21) Appl. No.: 14/750,724

(22) Filed: Jun. 25, 2015

(65) Prior Publication Data
US 2016/0378297 A1    Dec. 29, 2016

(51) Int. Cl.
*G06F 3/048* (2013.01)
*G06F 3/0481* (2013.01)
*G06F 3/0484* (2013.01)

(52) U.S. Cl.
CPC ...... *G06F 3/04817* (2013.01); *G06F 3/04842* (2013.01); *G16H 10/60* (2018.01); *G16H 15/00* (2018.01); *G16H 80/00* (2018.01)

(58) Field of Classification Search
CPC .. G06F 3/04817; G06F 3/04842; G06F 19/30; G06F 19/32; G06F 19/36; G06Q 50/24; G16H 10/60; G16H 15/00; G16H 80/00
See application file for complete search history.

(56) References Cited

U.S. PATENT DOCUMENTS

| | | | | |
|---|---|---|---|---|
| 6,836,780 B1 * | 12/2004 | Opitz | ............... | G06F 8/38 |
| 6,877,007 B1 * | 4/2005 | Hentzel | ............... | G06Q 30/02 707/999.01 |
| 7,487,438 B1 * | 2/2009 | Withers | ............... | G06K 9/00449 382/151 |
| 7,941,525 B1 * | 5/2011 | Yavilevich | ............... | G06Q 30/02 709/203 |
| 2005/0065823 A1 * | 3/2005 | Ramraj | ............... | G06F 19/322 705/3 |
| 2008/0184102 A1 * | 7/2008 | Selig | ............... | G06F 17/243 715/234 |
| 2008/0208630 A1 * | 8/2008 | Fors | ............... | G06Q 50/24 705/3 |
| 2009/0158090 A1 * | 6/2009 | Bauchot | ............... | G06F 11/1441 714/15 |
| 2010/0094657 A1 * | 4/2010 | Stern | ............... | G06F 19/322 705/3 |
| 2010/0095208 A1 * | 4/2010 | White | ............... | G06F 17/30905 715/704 |
| 2012/0215560 A1 * | 8/2012 | Ofek | ............... | G06F 19/322 705/3 |
| 2013/0132833 A1 * | 5/2013 | White | ............... | G06F 3/048 715/704 |
| 2013/0227457 A1 * | 8/2013 | Kim | ............... | G06F 9/4443 715/769 |
| 2013/0238966 A1 * | 9/2013 | Barrus | ............... | G06K 9/00449 715/223 |

(Continued)

*Primary Examiner* — Patrick F Riegler
(74) *Attorney, Agent, or Firm* — Jones Day

(57) ABSTRACT

A platform is provided to capture data displayed on a screen of a graphical user interface. The platform can find relevant foreground windows and determine whether the windows belong to a monitored process. The platform can also identify the context of the screen and record any changes. Related system, method, apparatus, and non-transitory computer readable medium are also provided.

20 Claims, 23 Drawing Sheets

(56) References Cited

U.S. PATENT DOCUMENTS

| | | | | |
|---|---|---|---|---|
| 2013/0326386 A1* | 12/2013 | Vendrell | ............... | G06F 19/321 |
| | | | | 715/771 |
| 2014/0115712 A1* | 4/2014 | Powell | ................ | G06F 21/6263 |
| | | | | 726/26 |
| 2014/0215301 A1* | 7/2014 | Stone | .................... | G06F 17/248 |
| | | | | 715/225 |
| 2014/0215495 A1* | 7/2014 | Erich | ................... | G06F 11/3438 |
| | | | | 719/318 |
| 2014/0221836 A1* | 8/2014 | Takeda | ................... | A61B 8/463 |
| | | | | 600/443 |
| 2014/0249833 A1* | 9/2014 | Conti | ............... | G06Q 10/06316 |
| | | | | 705/2 |
| 2014/0258826 A1* | 9/2014 | Barrus | ............... | G06Q 10/0633 |
| | | | | 715/224 |
| 2015/0091331 A1* | 4/2015 | Takei | ................... | B62D 25/081 |
| | | | | 296/192 |
| 2015/0178252 A1* | 6/2015 | Dunn | ................. | G06F 17/2247 |
| | | | | 715/234 |
| 2015/0332011 A1* | 11/2015 | Ting | ..................... | G06F 19/327 |
| | | | | 705/2 |
| 2015/0339038 A1* | 11/2015 | Illobre | ............... | G06F 3/0481 |
| | | | | 715/835 |
| 2016/0232298 A1* | 8/2016 | Campbell | ............. | G06F 19/322 |

* cited by examiner

SMART DISPLAY DATA CAPTURING PLATFORM FOR RECORD SYSTEMS

TECHNICAL FIELD

The subject matter described herein relates to a platform for extracting data displayed on a user interface, particularly, from an electronic medical record (EMR) system.

BACKGROUND

Electronic health record (ERR) and electronic medical record (EMR) systems have been widely embraced by medical facilities and providers. (EHR and EMR will be referred to interchangeably herein.) For example, EMR is the principal information system at many hospitals that allows the healthcare provider to read in real-time medical information from the EMR, and (for example) enter diagnosis, treatment plan for a patient. Although some EMRs provide a way for its data to be distributed or queried by third party providers, there is generally a significant latency in getting the information. For example, if a doctor enters an update or orders and exam for a patient in the EMR, it can take several minutes for that update or order to reach a third party provider. This latency/delay can be unacceptable in some instances as in can, for example, delay care or result in medical error if a change in the order is not timely received.

Furthermore, not all clinical information is available via the native EMR distribution mechanisms mentioned above. For example, in many EMR, the healthcare provider can define unique screens and fields that are not part of the standard screens and fields provided by the standard EMR distribution. Often, those proprietary fields are not made available by the EMR to third party applications.

SUMMARY

Variations of the current subject matter are directed to methods, systems, devices, and other articles of manufacture that are provided to assist the project manager in managing a project in a project management platform.

In some variations, the current subject matter provides a method for reading a screen of a graphical user interface. The method includes receiving the screen having a plurality of windows (each of the windows can include one or more GUI elements), and determining whether each of the windows belong to a monitored process. The method also includes determining whether each of the windows match a configured window to generate a list of possible matching windows, and matching the GUI elements of the possible matching windows to a set of configured elements. The method further includes detecting a change to one of the GUI elements of the possible matching windows; and storing the change of one of the GUI elements of the possible matching windows.

In some variations, the change is stored temporarily at a local computer terminal where the screen is displayed to the user.

In some variations, the method can further include detecting, using at least one data processor, a trigger event, and when the trigger event is detected, storing, using at least one data processor, the change in long-term data storage. In some variations, the change is stored in long-term data storage only when the trigger event is detected.

In some variations, the method further includes listening for a new screen, and determining whether the new screen concerns the same patient as the screen.

In some variations, the screen was transmitted using HTML. In some variations, the screen includes data from an electronic medical record system.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The subject matter described herein provides many advantages. For example, by running the current subject matter in the background of existing EMR terminals, the user experience of the EMR will not be changed (no new training is required). Also, the EMR system itself will not need to be changed. At the same time, updates and user input into the EMR can be captured in real-time (or near instantaneously) to minimize any latency and/or delays. The current subject matter can also seamlessly integrate two or more different EMR systems without the need to actually integrate the underlying data at the backend.

BRIEF DESCRIPTION OF THE FIGURES

FIGS. 13-23 are graphical illustrations of additional features of the current subject matter.

DESCRIPTION

Figure 1:
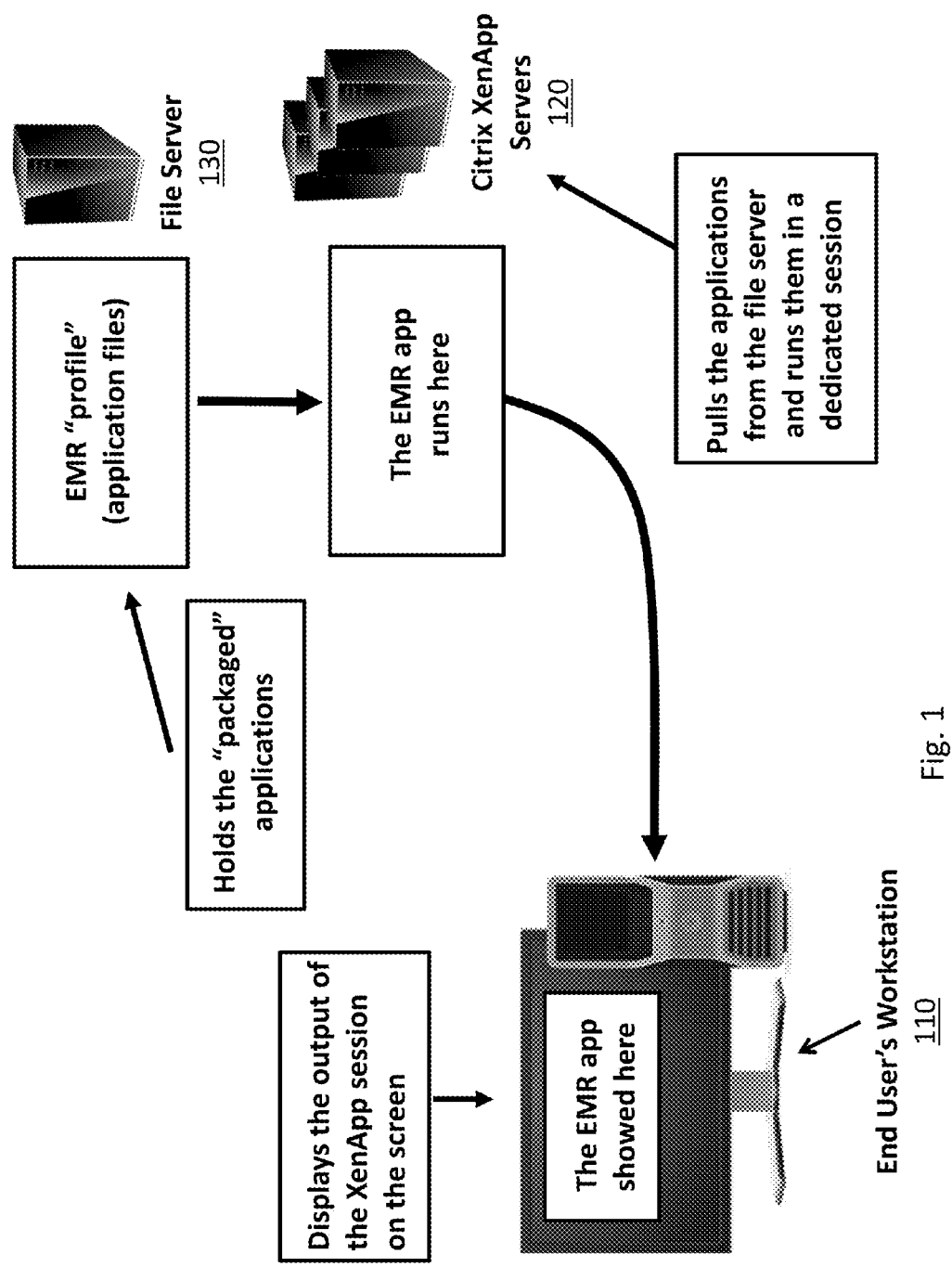
FIG. 1 is a diagrammatic illustration of an example of an existing EMR system implementation.

FIG. 1 is a diagrammatic illustration of an example of an existing EMR system implementation. The system generally includes a plurality of end user workstations 110 that provides a user interface for interacting (e.g., display outputs and receive inputs) with the data in the EMR. Typically, the end user workstations function simply as remote terminals for accessing data that is stored and/or processed elsewhere. The system also generally include one or more app servers 120 where the EMR application runs, and one or more file servers 130 that stores the application files/data. In this example, the PAR app is run on one or more Citrix XenApp servers, and the end user workstation 110 displays the output of the XenApp session on the screen. The file server 130 generally holds the application files/data (e.g., EMR "profile") and the "packaged" applications while the App Server 120 pulls the applications from the ilk server and runs them in a dedicated session. The exactly type of App server and file server is not important; other systems can be used.

Figure 2:
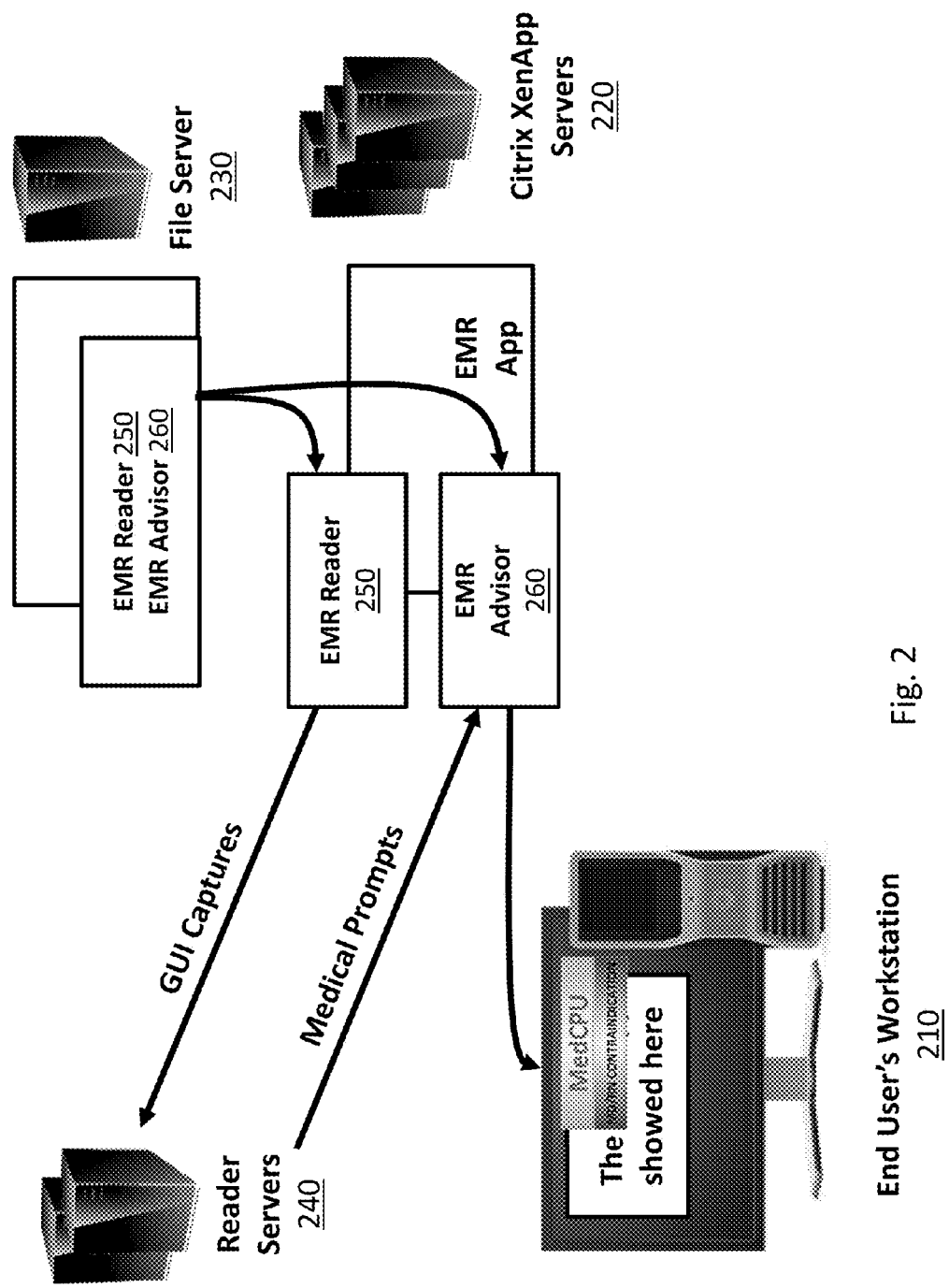
FIG. 2 is a diagrammatic illustration of an example of a variation of the current subject matter.

FIG. 2 is a diagrammatic illustration of an example of an implementation of the current subject matter. Here, the end user workstation 210, App Server 220, and File Server 230 are essentially the same as those shown in FIG. 1. The difference is that one or more Reader Servers 240 are provided. The one or more Reader Servers 240 can be configured to run one or more applications including, for example, EMR Reader 250, and EMR Advisor 260.

The EMR Reader 250 operates in the background to capture one or more data from the graphical user interface (GUI) displayed on the end user workstation 210. In essence, the EMR Reader 250 captures the GUI and sends the relevant data to the Reader Server(s) 240.

In some variations, the EMR Reader process can be launched when a user session opens at the end user workstation. This can be done, for example, by deploying a proprietary Windows service that injects a Reader and/or Advisor to every new Windows session (or similar operations in other operating systems).

Figure 3:
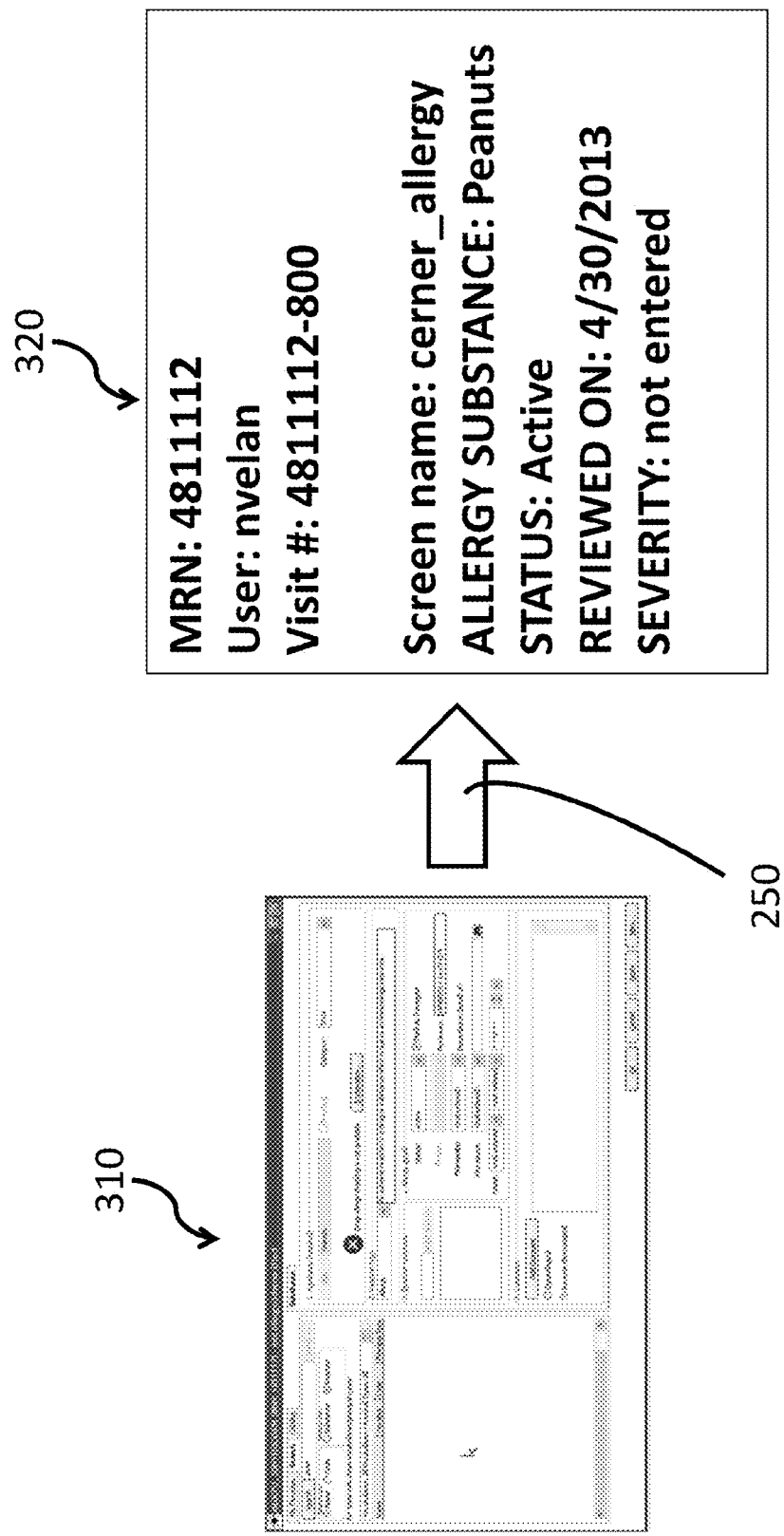
FIG. 3 depicts an example of the type of information that can be captured by an EMR Reader of a variation of the current subject matter.

FIG. 3 depicts an example of the type of information that can be captured by the EMR Reader. Here, a computer screen 310 is shown at an end user workstation displaying medical data from an EMR. By using the EMR Reader in accordance with the current subject matter, medical data 320 can be extracted.

Figure 4:
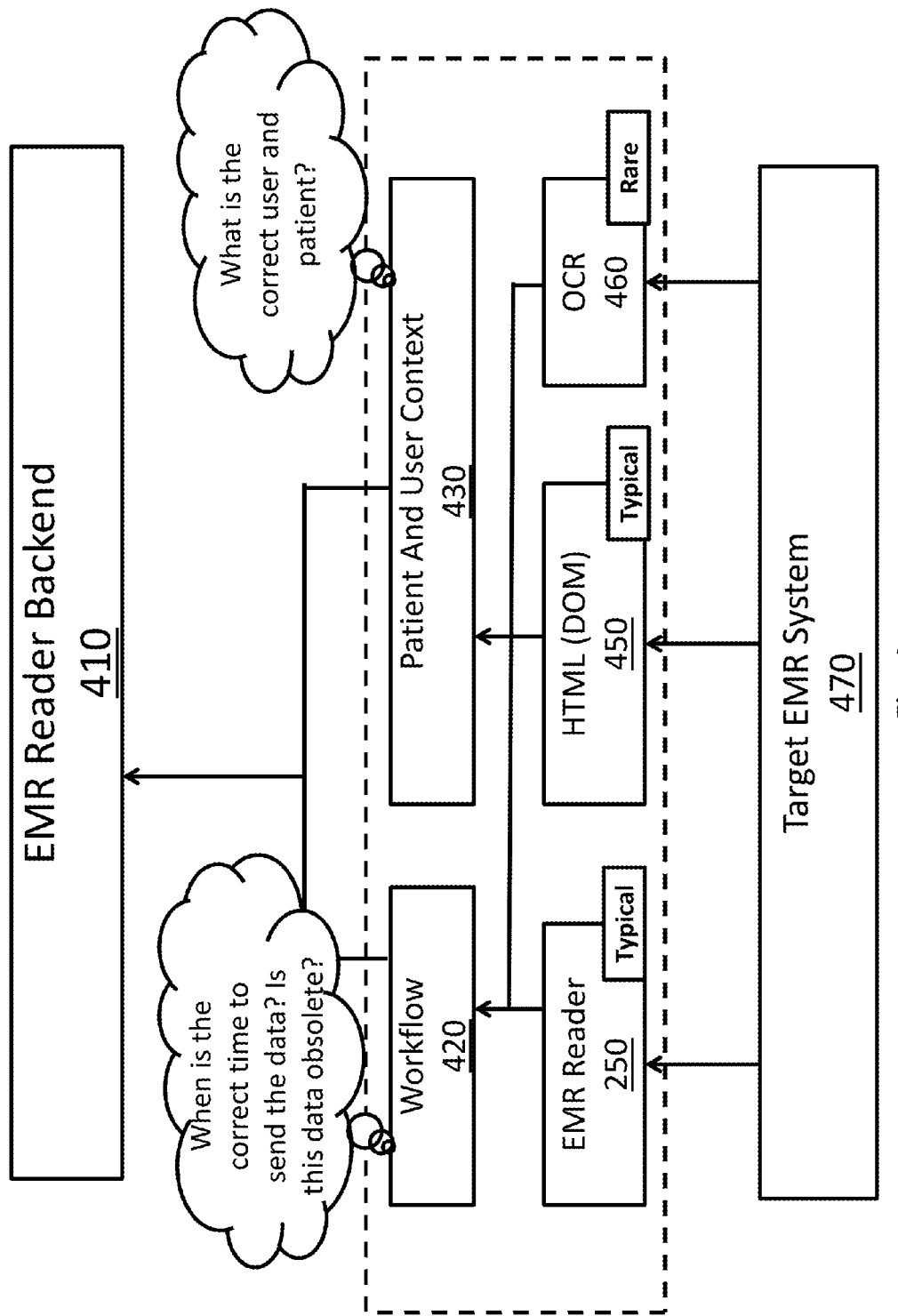
FIG. 4 is a diagrammatic view of an EMR Reader platform of a variation of the current subject matter.

FIG. 4 depicts a diagrammatic view of the EMR Reader platform. Typically, data from a Target EMR System 470 can be accessed via an EMR Reader 440 operating in the background of the end user workstation, or via an HTML (DOM) 450 if the EMR is accessed via, for example, a web application. In some cases, however, the data from the target EMR system needs to be obtained through OCR (optical character recognition) 460. In some variations, the OCR can take a screenshot of the entire screen or a certain area of the screen, and parse and analyze what's on the screen to obtain the data.

In any event, the data can be processed by Workflow 420 as will be discussed in more detail below. Among other features, Workflow 420 can answer questions such as "when is the correct time to send the data? And/or "is this data obsolete?" The data can also be processed by Patient and User Context 430 as will also be discussed in more detail below. Among other features, Patient and User Context 430 can answer questions such as "what is the correct user and patient," which is especially important in the case of medical records.

Figure 5:
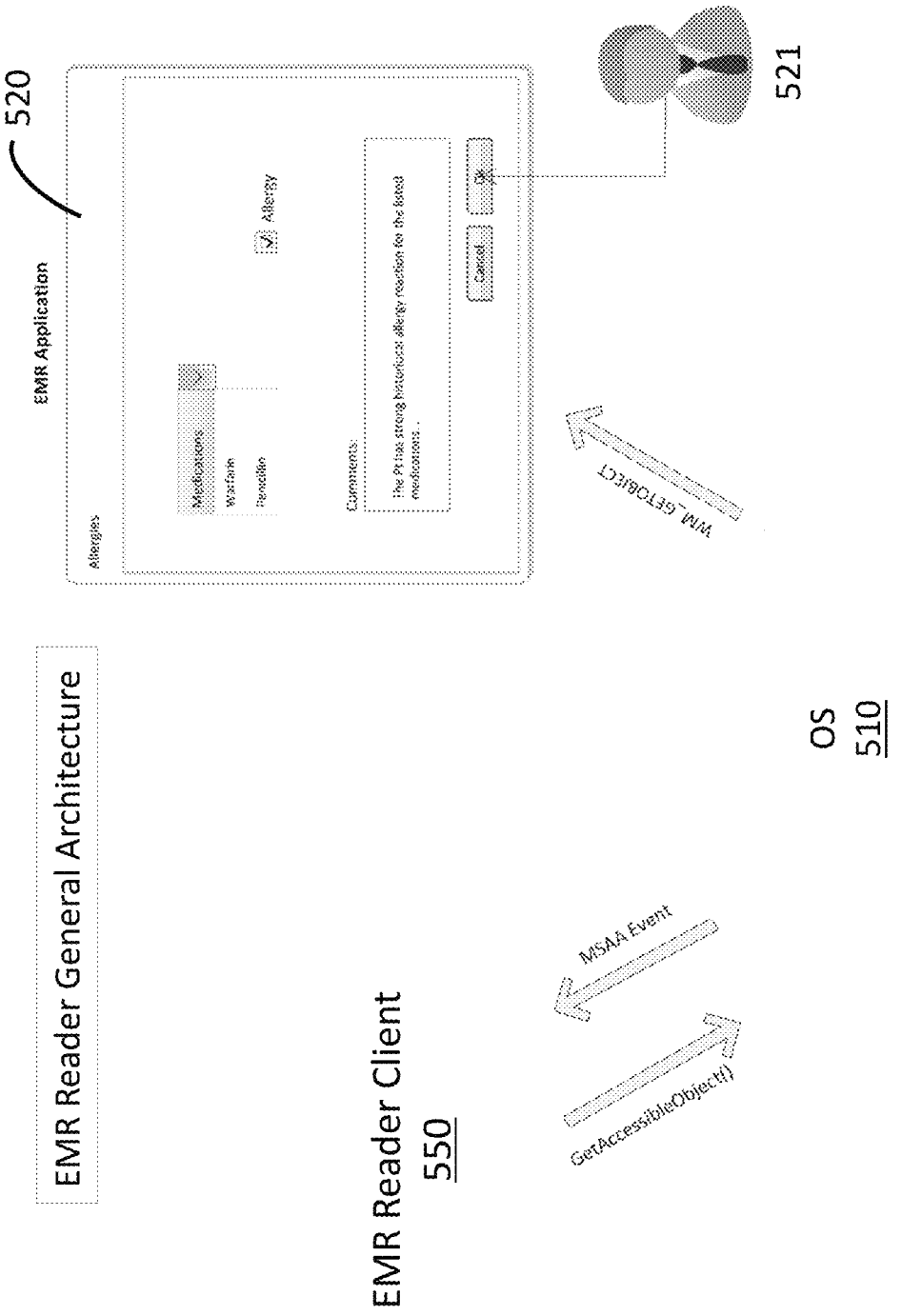
FIG. 5 is a diagrammatic illustration of a general architecture of an example of EMR Reader in accordance with the current subject matter.

FIG. 5 is a diagrammatic illustration of the general architecture of an example of EMR Reader in accordance with the current subject matter. As shown, an EMR Reader Client 550 is in communication with the operating system (OS) 510 (e.g., the Windows OS) which is providing a graphical user interface (GUI) of EMR Application 520 to a user 521. The EMR Reader Client 550 can be run in the background, and "listens" to the information being displayed and/or entered on the computer display or screen. This allows the EMR Reader to obtain the data without direct access or communication with the EMR system itself.

In some variations, when operating in DOM (HTML) reading mode, the EMR Reader can access the embedded browser in the EMR using, for example, a standard COM API provided by the browser.

Figure 6:
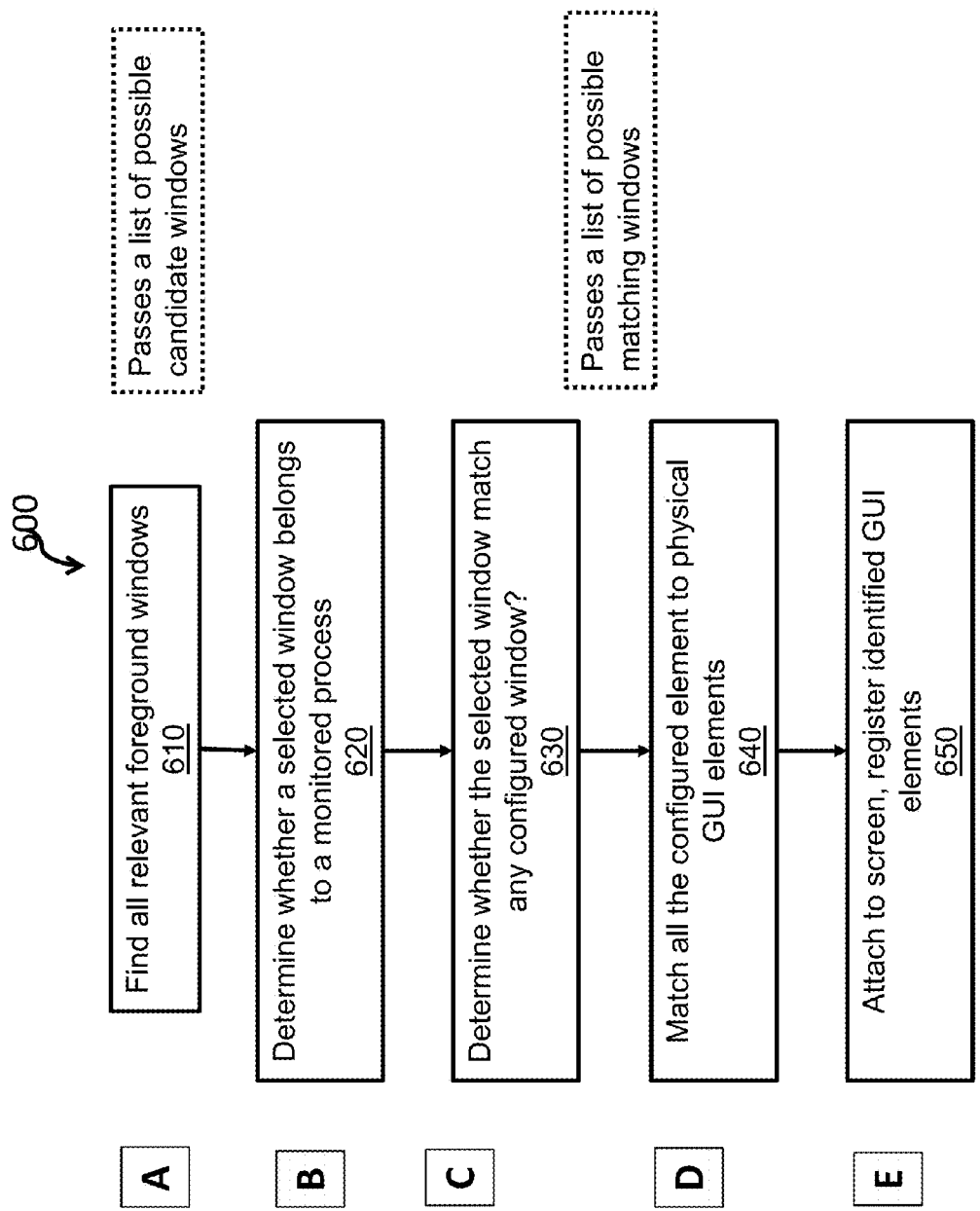
FIG. 6 depicts a process flow of an example of an EMR Reader in accordance with the current subject matter.

FIG. 6 depicts a process flow 600 of an example of an EMR Reader in accordance with the current subject matter (Workflow 420 in FIG. 4). References will also be made to FIGS. 7-20 which illustrate various features of the workflow.

Figure 7:
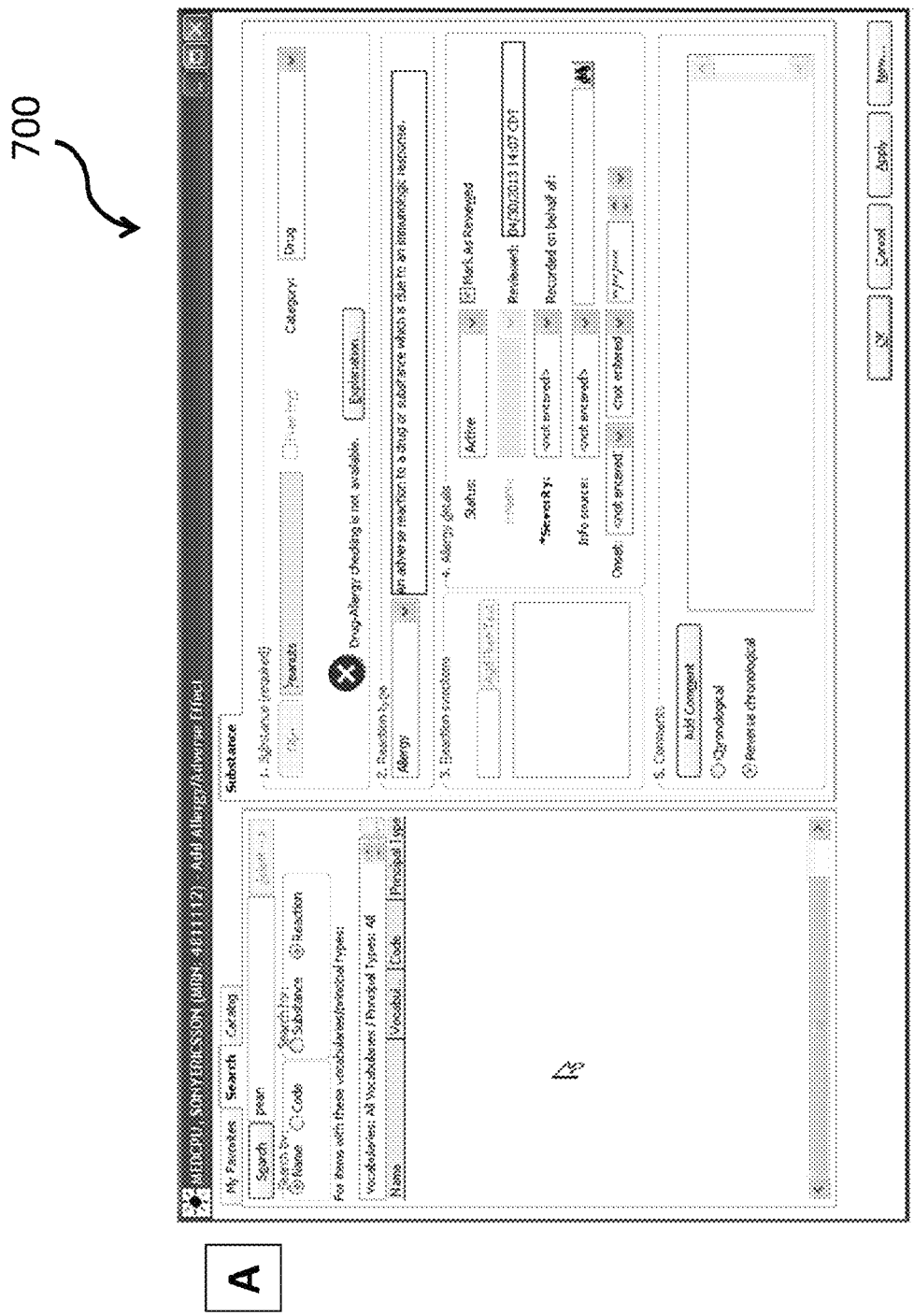
FIG. 7 depicts an example of a screen displayed on an end user workstation.

FIG. 7 depicts an example of a screen 700 displayed on an end user workstation. Screen 700 contains data in an EMR system. The screen 700 can be, for example, a default screen, or a screen that is displayed as a result of prior user action. In this case, screen 700 is displaying various medical data selected by the end user for a particular patient. When the screen is first opened, the EMR Reader will recognize an EMR event and begins the workflow process 600.

Figure 8:
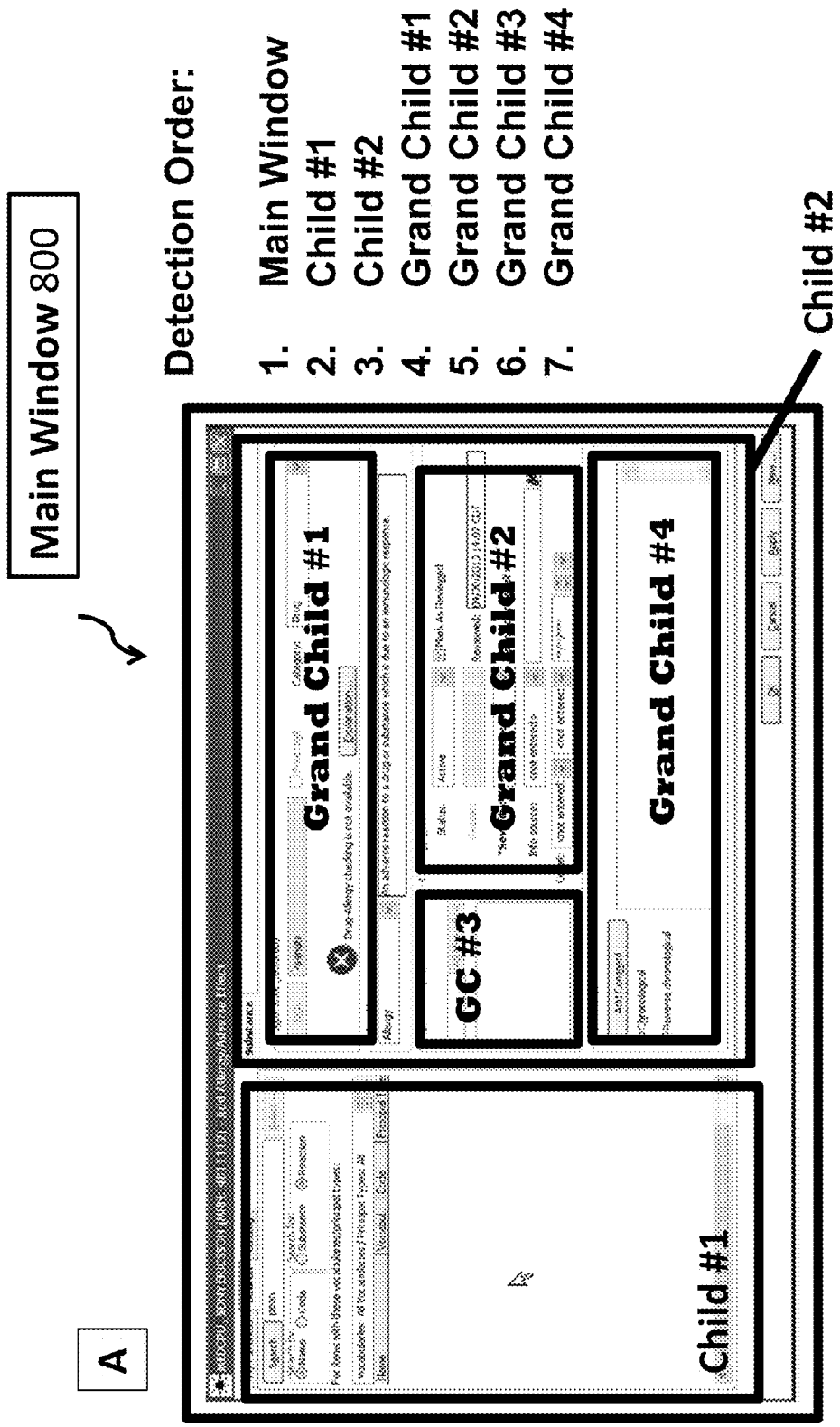
FIG. 8 is a graphical illustration of how the screen shown in FIG. 7 can be divided in accordance with some variations of the current subject matter.

At 610, the EMR Reader will find all relevant foreground window(s). Referring to FIG. 8, screen 700 includes a main window 800, which includes Child #1 on the left, and Child #2 on the right. Child #2 includes Grand Children #1-#4. In some variations, the windows are detected in the order of largest to smallest. Other detection orders can be implemented.

In some variations, the hierarchy (main window, children, and grand children, etc.) can be presented in the operating system (OS) as child-parent relationship between OS Window objects (for example).

In some variations, in the DOM (HTML) reading mode, the hierarchy can be more directly represented, tier example, as child-parent relationship between different nodes in the DOM tree.

In the FIG. 8 example, there are three levels of hierarchy from the main window to the children and grandchildren. Fewer or additional levels of hierarchy are possible. For example, the grandchildren can have additional grand grandchildren, and so on.

In some variations, the main window is divided into children/grandchildren to match corresponding window configurations in the EMR. This can be particular useful because in some variations of EMRs, a particular window can be reused different screens, hut can be located in different locations and/or have different particular features (e.g., based on user configuration).

At 620, the EMR Reader determines whether a selected window belongs to a monitored process. In some variations, the EMR Reader determines this for each of the windows (e.g., the main windows, children, grandchildren, etc.). For example, Screen 700 is a screen that enables the user to enter data (e.g., text field for "Substance," a drop-down menu for "Reaction Type," etc.). This means that the EMR Reader needs to monitor any changes made to this screen and capture user input.

In some variations, a screen can contain passive data that should be captured. The EMR Reader can be configured to capture those data, for example, immediately or within a certain period automatically. In some variations, the EMR Reader can be configured to capture those data whenever a change in the data occurs.

If at least one window belongs to a monitored process (as is the case for Screen 700), at 630, the EMR Reader determines whether the selected window match any configured window. Here, a configured window is a known window in the EMR system.

Figure 23:
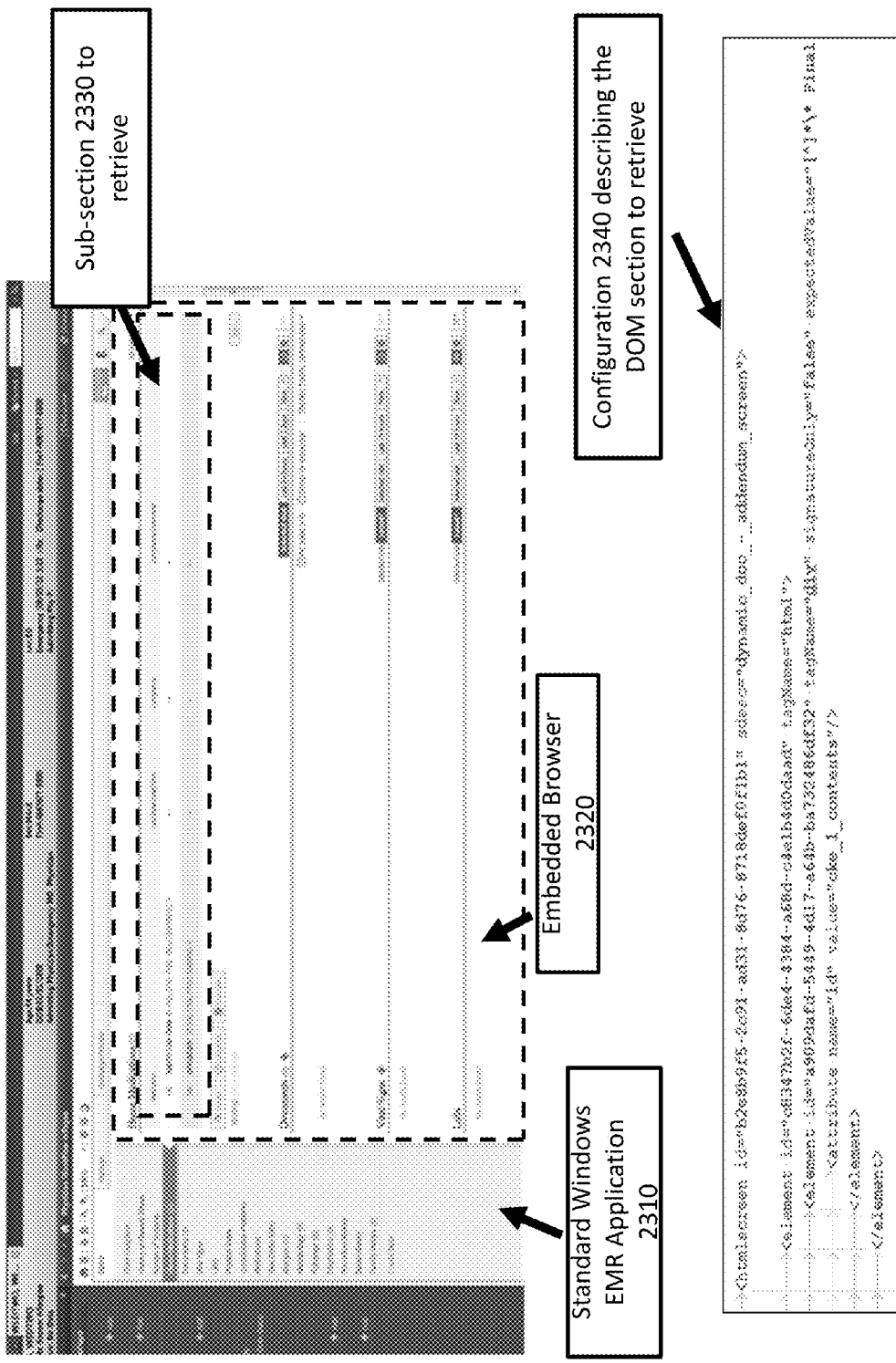

For HTML screens (see, for example, FIG. 23), these are often embedded within a standard OS window, and the determination whether the window belongs to the EMR process can be done in similar (e.g., identical) manner. In some variations, the entire EMR can be run from a browser, in which case any browser window is a potential EMR window. For example, FIG. 23 depicts examples of an HTML screen that contains windows (e.g., standard windows) of an EMR application 2310. The screens are displayed via an embedded browser 2320. Here, the screen contains sub-section 2330 to be retrieved and corresponding configuration data 2340 describing the DOM section to be retrieved.

Figure 9:
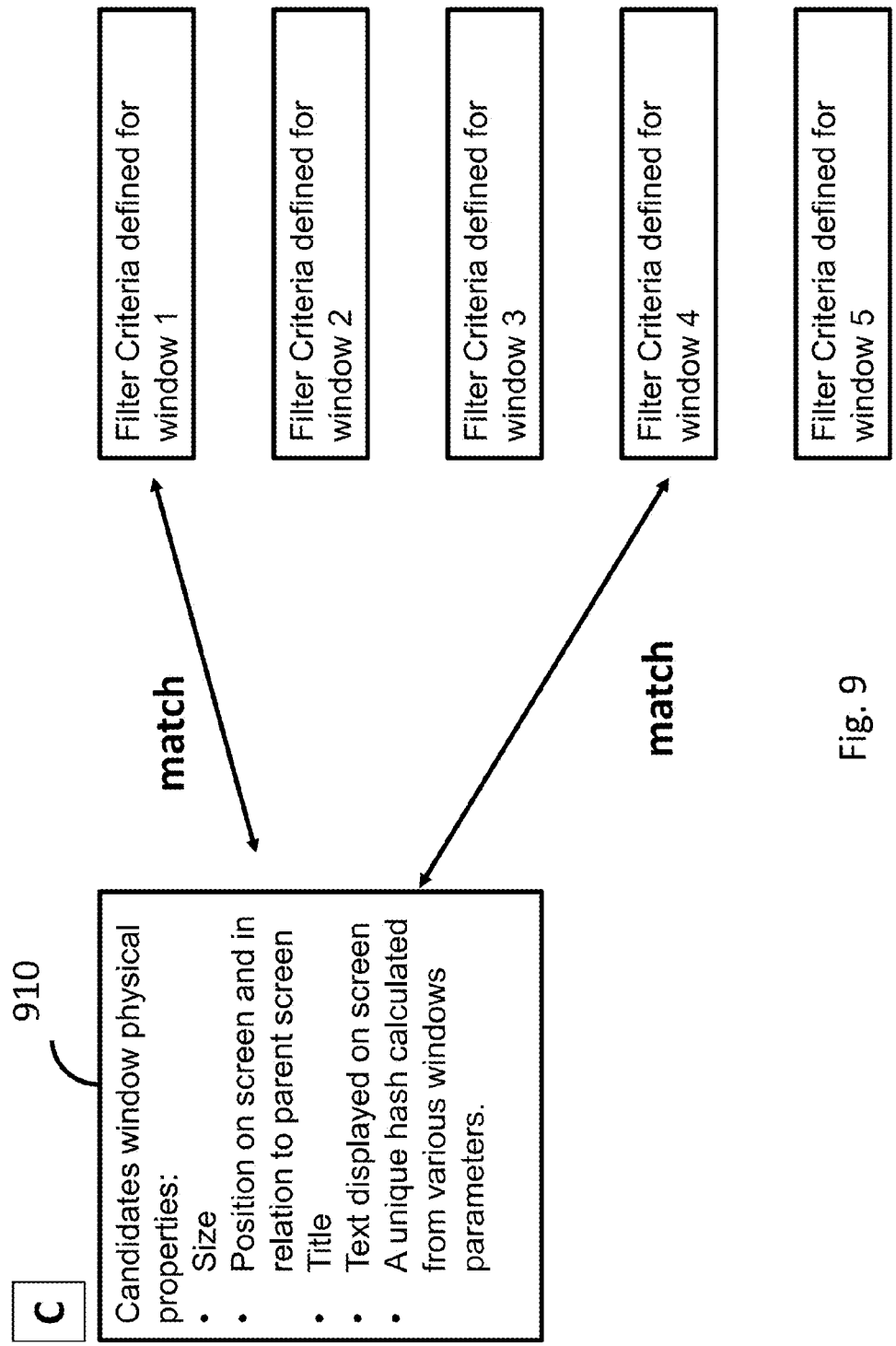
FIG. 9 is a graphical illustration of some features of the current subject matter.
Figure 10:
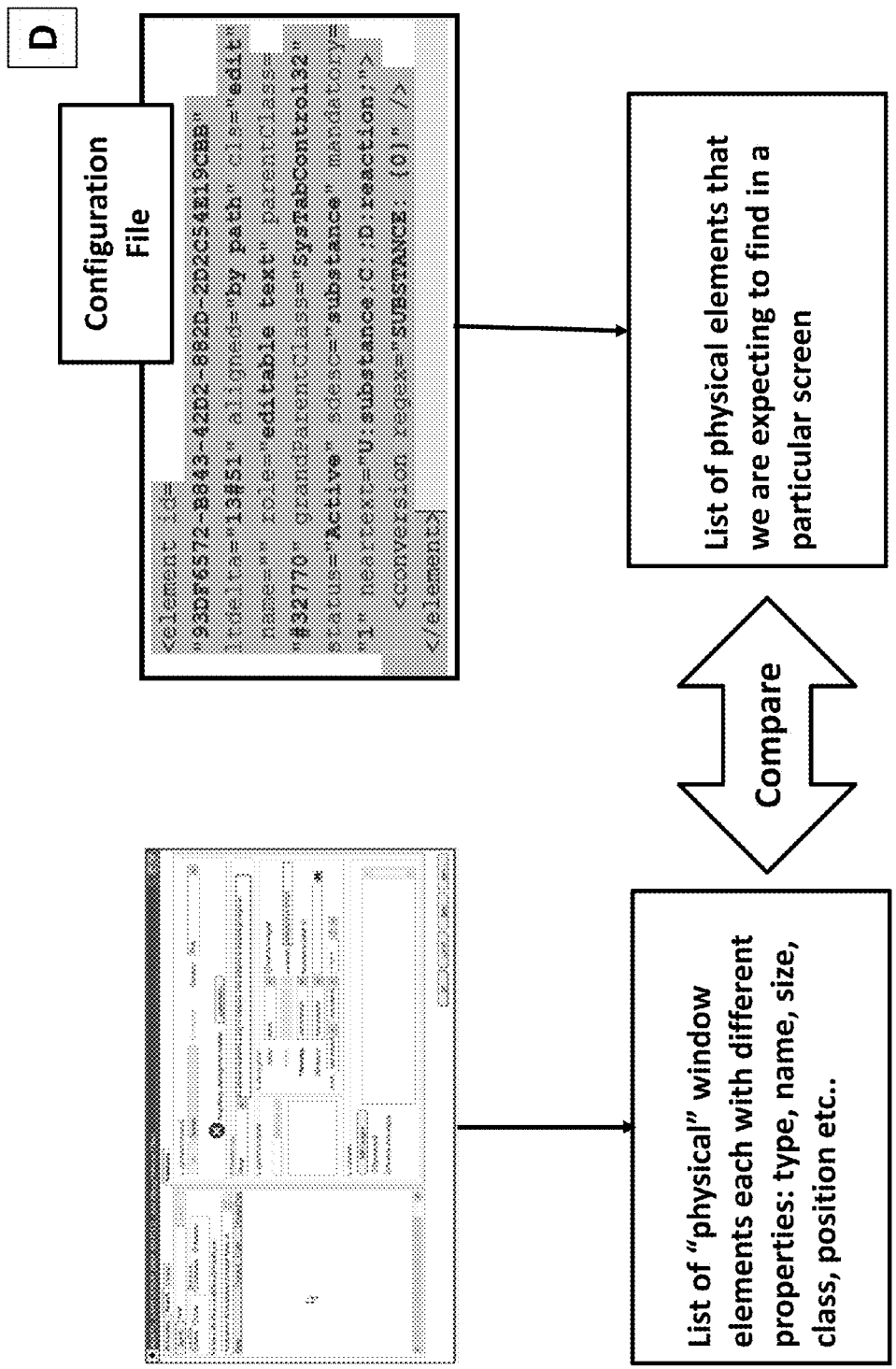
FIG. 10 is another graphical illustration of some features of the current subject matter.

As shown in FIG. 9, candidates 910 for determining whether the selected window matches any configured window include one or more of for example, window physical properties such as size, position on screen (and/or in relation to parent screen), title, text displayed on screen, and a unique hash calculated from various windows parameters. By checking one or more of these criteria, a matching configured window (e.g., from any of windows 1-5) can be determined. In some variations, a list of possible matching windows can be passed (e.g., for further processing). For HTML-based screens, the matching criteria can be, for example, specific patterns in the HTML text/DOM representation of that HTML. For example, the existence of certain HTML tag IDs, or specific paths within the HTML (e.g., the tag third <DIV> in the tag <BODY> has a class property of "bold").

Once a match is found for the selected window, the EMR Reader can match one or more (e.g., all) the configured elements of the matching configured window to one or more physical GUI elements in the selected window. For example, referring to FIG. 10, a list of "physical" window elements and the corresponding properties such as type, name, size, class, position, etc., can be compared with a list of physical elements that can be expected to be found in a particular screen from the configuration file (for example) of the EMR.

In some variations, a single foreground displayed physical window can be broken down into sub-regions, each of which can be matched with configured screens. For example, the EMR Reader can employ a top-down comparison approach that starts with the main screen and traverses all the sub-regions until everything that can be matched does in fact match.

Figure 11:
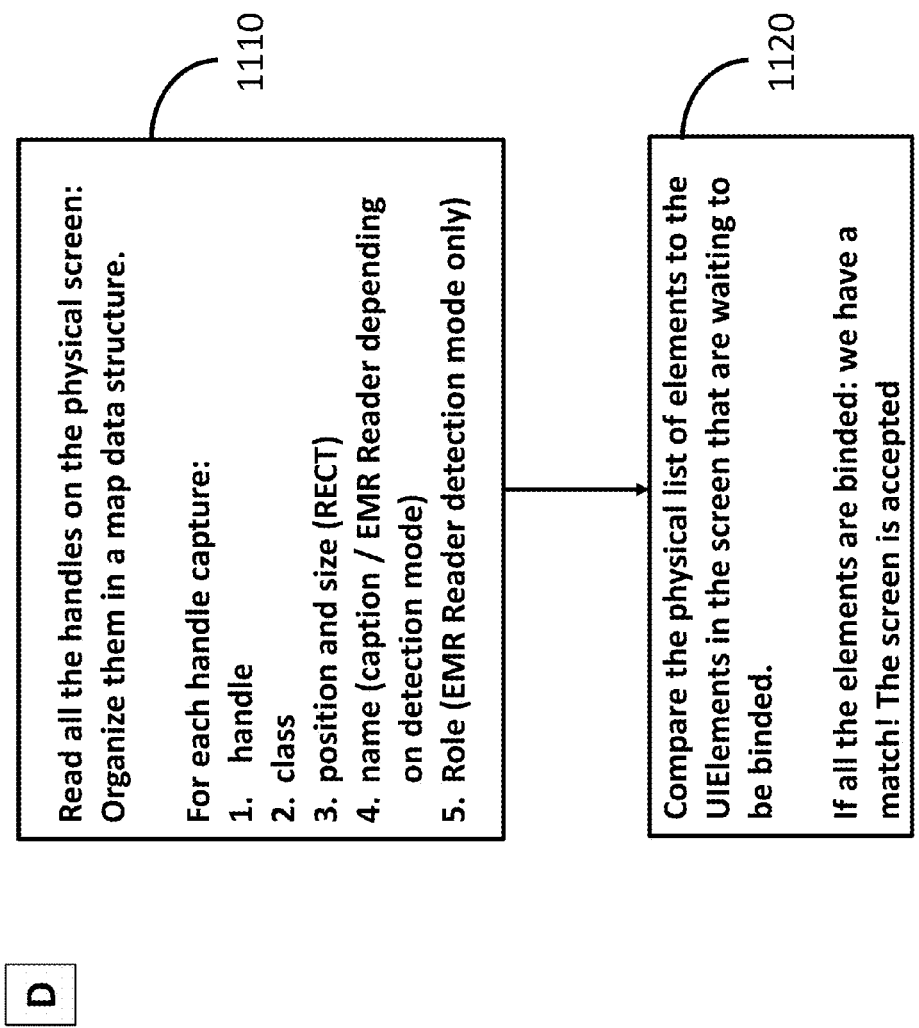
FIG. 11 is a process flow diagram of certain features of the current subject matter.

Referring to FIG. 11, the EMR Reader can read all the handles on the physical screen (e.g., organize them in a map data structure). For each handle capture, one or more characteristics such as window class, position and size (RECT), caption, and accessibility properties such as name or role. The handles on the physical screen can be compared with the physical list of elements to the UI (user interface) elements in the screen that are waiting to be binded (will be discussed in more detail below). In some variations, if all the elements are binded, then there is a match. The screen is accepted (1120).

In some variations, the Reader generates a list of physical GUI elements that are currently displayed on the screen (e.g., text boxes, lists, combo boxes, etc.). The Reader can be configured to determine which of these elements are relevant (e.g., containing data to be read from and/or recorded), and in some variations, which that are not relevant. In some variations, the elements are no initially "binded" (e.g., have not been determined as relevant for reading, or if an object has not been created in the Reader to track them).

In some variations, "binding" includes a process of creating an object in the reader memory and have it "spy" on the physical element on the screen for any changes in data (the Reader Object and the physical object are "bound" together). This can be done, for example, by keeping a record of the physical GUI element's Window handle which can be a number (for example) assigned to each GUI element in the Windows operating system.

In some variations, in DOM (HTML) reading mode, the internal memory object can be "binded" to a particular path and unique path in the DOM tree. The EMR Reader can then "spy" on that particular path by continuously asking for the value of that DOM element value from the attached browser.

In some variations in DOM (HTML) reading mode, it is also possible, for example, to configure the retrieval of an entire sub-section of the DOM as a block of "raw" HTML to be sent to the backend as is for further evaluation.

In some variations, while the Reader mode can be configured to retrieve the value of a single GUI element, the DOM (HTML) reading can be configured, for example, to send the complete HTML or a large part of the screen to be processed in the backend.

In some variations, the Reader can take one or more (including all) of the physical GUI elements and match them to, for example, a configuration element in an XML file to create a Reader internal object that is binded with the physical element. In some variations, this can be done, for example, by comparing a list of properties of a physical GUI element (e.g., windows class, position, name, etc.) to the configuration element(s) in the configuration (e.g., FIG. 12) and bind the element if there is a match. In some variations, if there is no match, then the Reader moves on to the next element.

Figure 12:
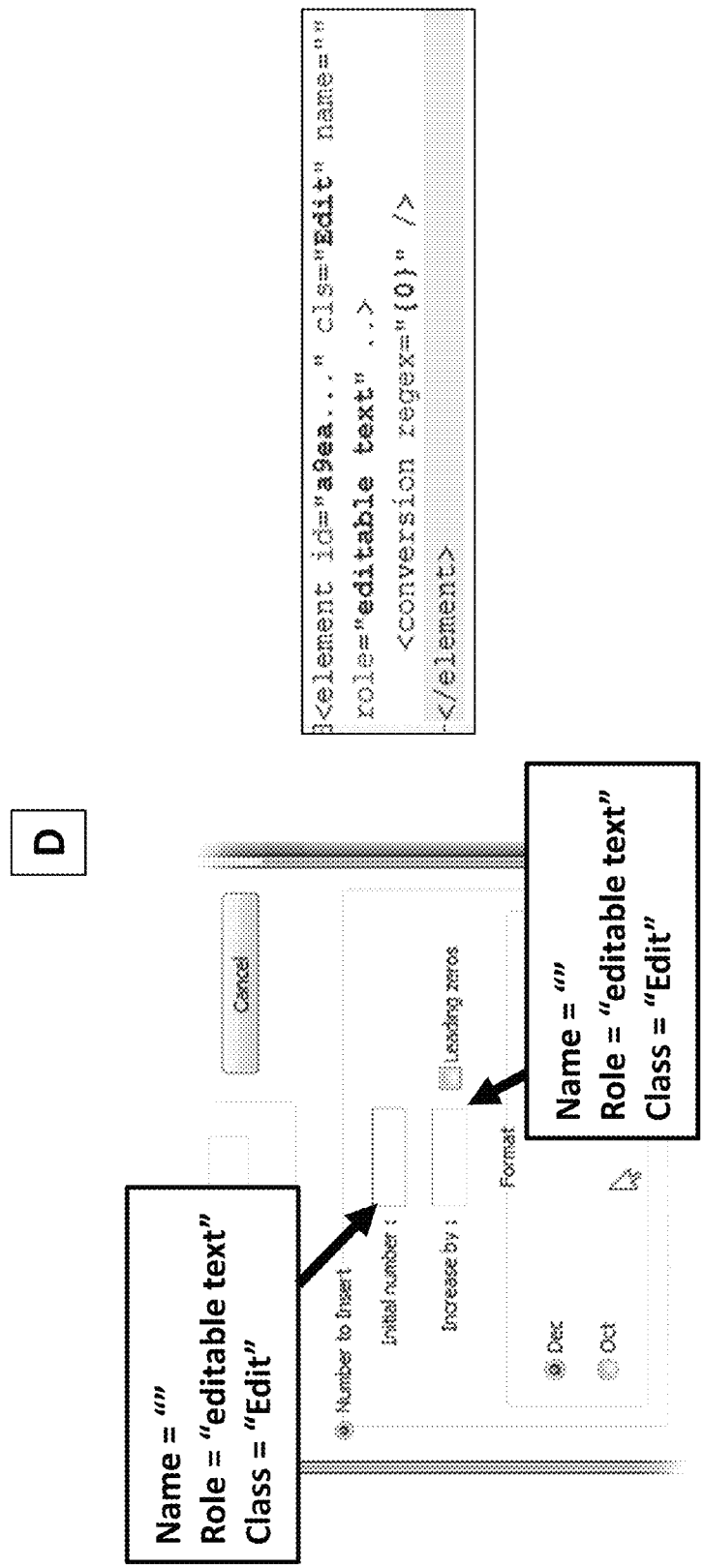
FIG. 12 depicts an example of GUI elements of a screen and the corresponding computer code.

FIG. 12 is a graphical illustration of the process shown in FIG. 11. On the left are fields (elements) of a window and their handles, which are being matched with the corresponding handles in the configuration file or backend data on the right.

FIGS. 13-18 show additional ways of matching physical GUI elements with configuration elements based on, for example, the physical element position in the parent window, and in relation to other GUI elements.

Sometimes, comparing the properties of a physical GUI element to the matching configuration element is enough and additional ways of matching are not required. For example, if there is only one GUI element that matches the criteria specified in the configuration (config) file, then no additional matching is needed. In some instances, however, the element properties are not enough for a match because not all elements are available and/or unique. For example, all "edit text" GUI elements are usually identical by all properties other than the location on the screen. In some variations, when there is no 1:1 match between the GUI elements on the screen and the config file, additional data such as the element position would need to be taken into account before performing the "binding."

Figure 13:
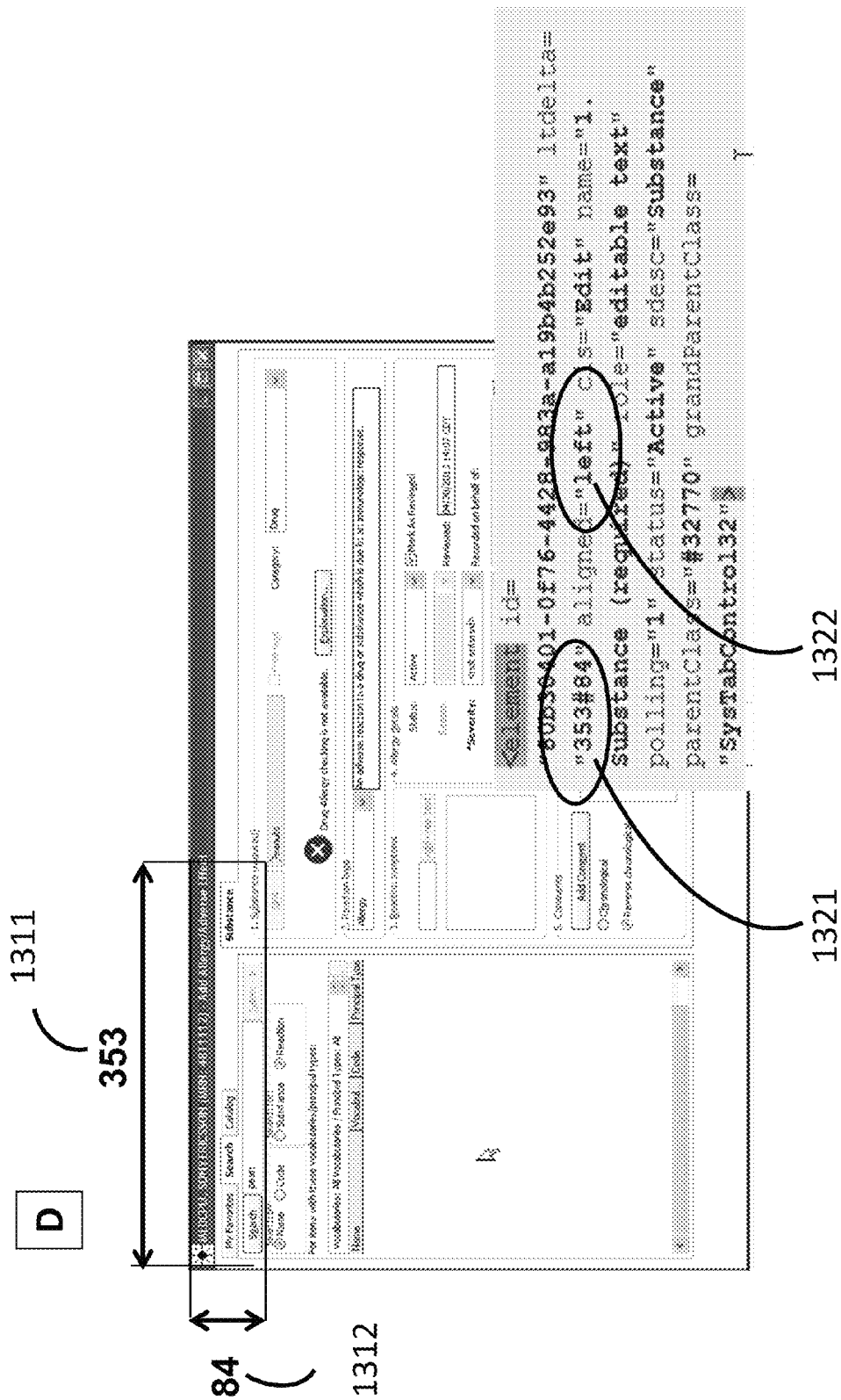

FIG. 13 is a graphical illustration of an example of how to define an element by position. Here, the distance in pixels (can include a tolerance) from the upper left corner of the screen. In the example provided the element GUI that displays the phrase "Peanuts" will be binded to configuration element displayed only if its distance from the window to the top left corner in pixels is 353 in the x direction and 84 in the y direction. In some variations, one or more other reference spots can be utilized. FIG. 13 shows the position and size (1311, 1312) of a window that are being matched with the corresponding data (1321, 3122) in the configuration file or backend data on the right.

Figure 14:
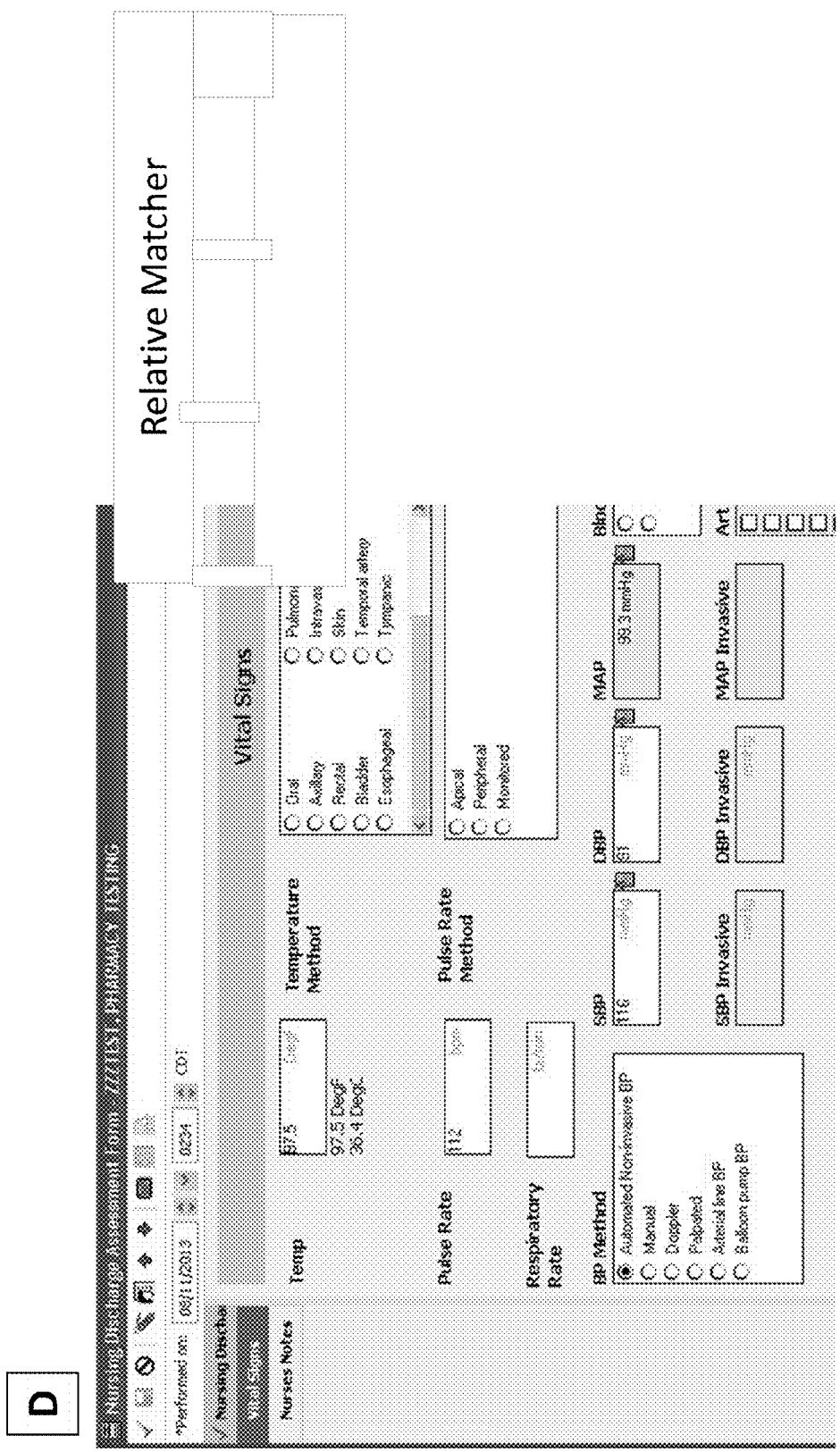
Figure 15:
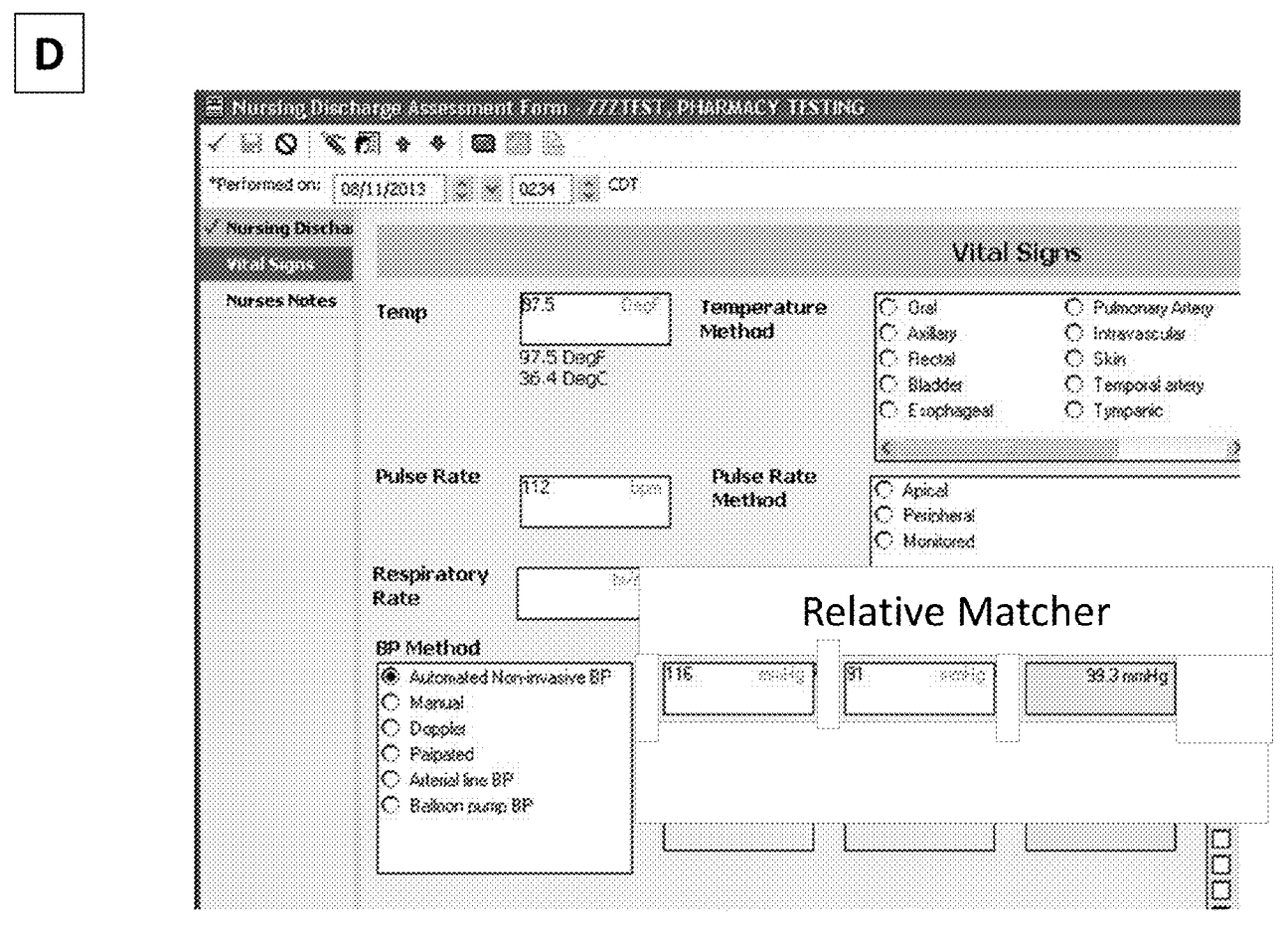
Figure 16:
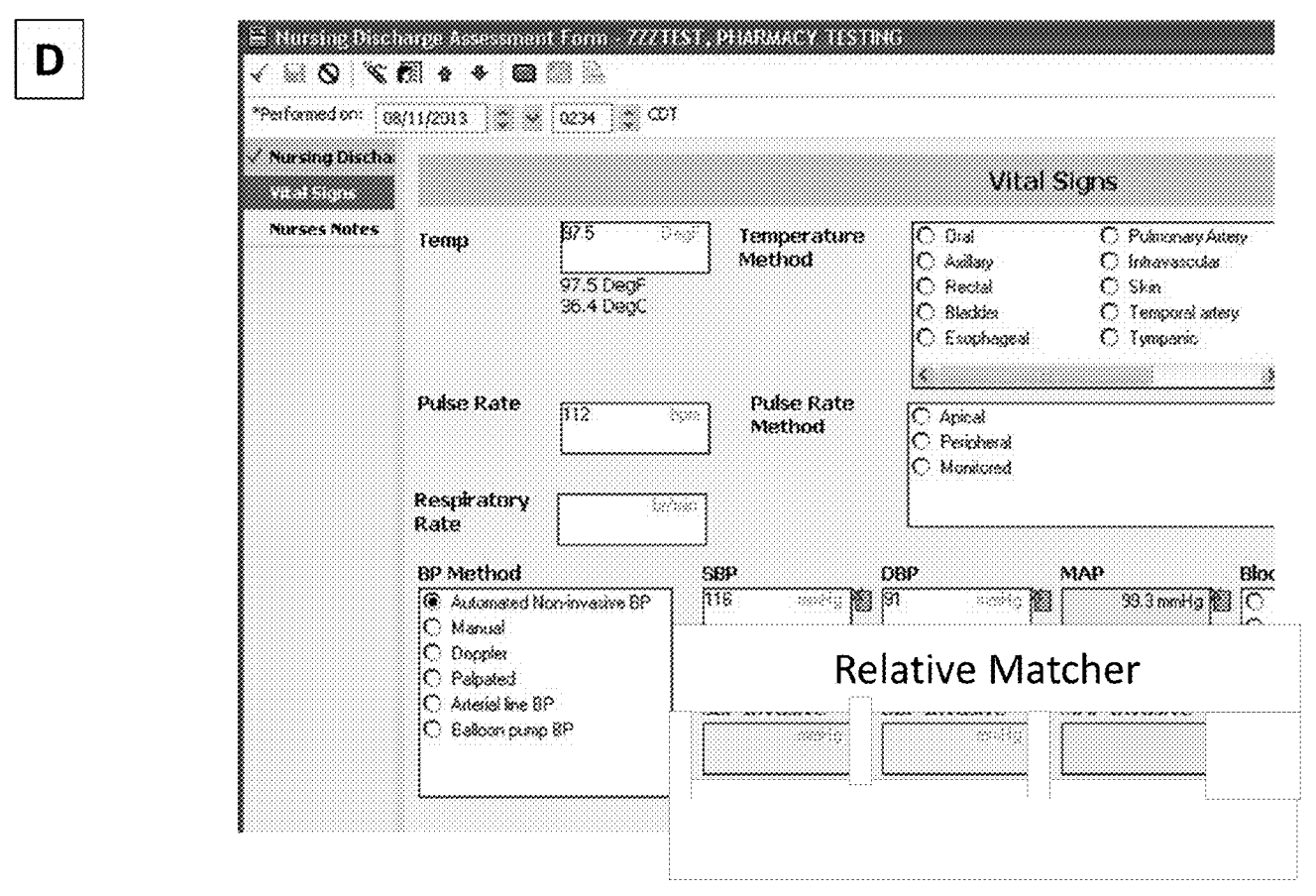

FIG. 14-16 shows an example of position matching that is more complex. In this position matching called "relative," the distance of the different elements from one another should be fixed. Instead of measuring the distance of each element from location like the window's top-left (for example), the Reader measures the relative distance(s) of the elements from one another. In some variations, this is as if the Reader is provided with a template with "cut-out holes" and the Readers tries to match all the elements together—if a group of elements all fit within the template, then they can be binded. In some variations, even if one element does not match the template, the entire group is discarded.

Figure 17:
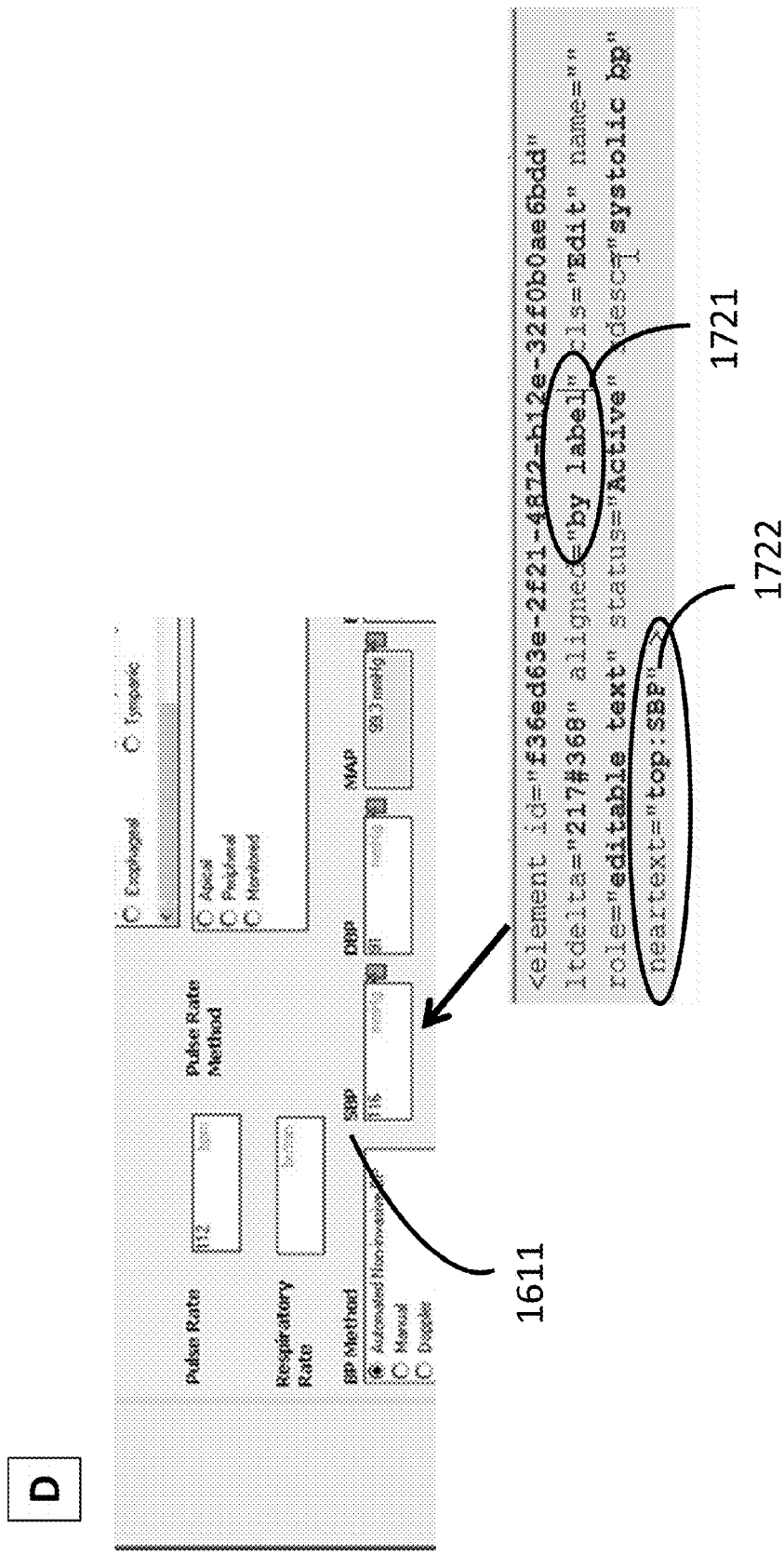

FIG. 17 shows a position matching that look for visible text labels on the screen. For example, here, the Reader looks for a text edit box that has a label with the text "SBP" directly above it (label 1611 of an element is being matched with the type and label (1721, 1722) in the configuration file or backend data).

Figure 18:
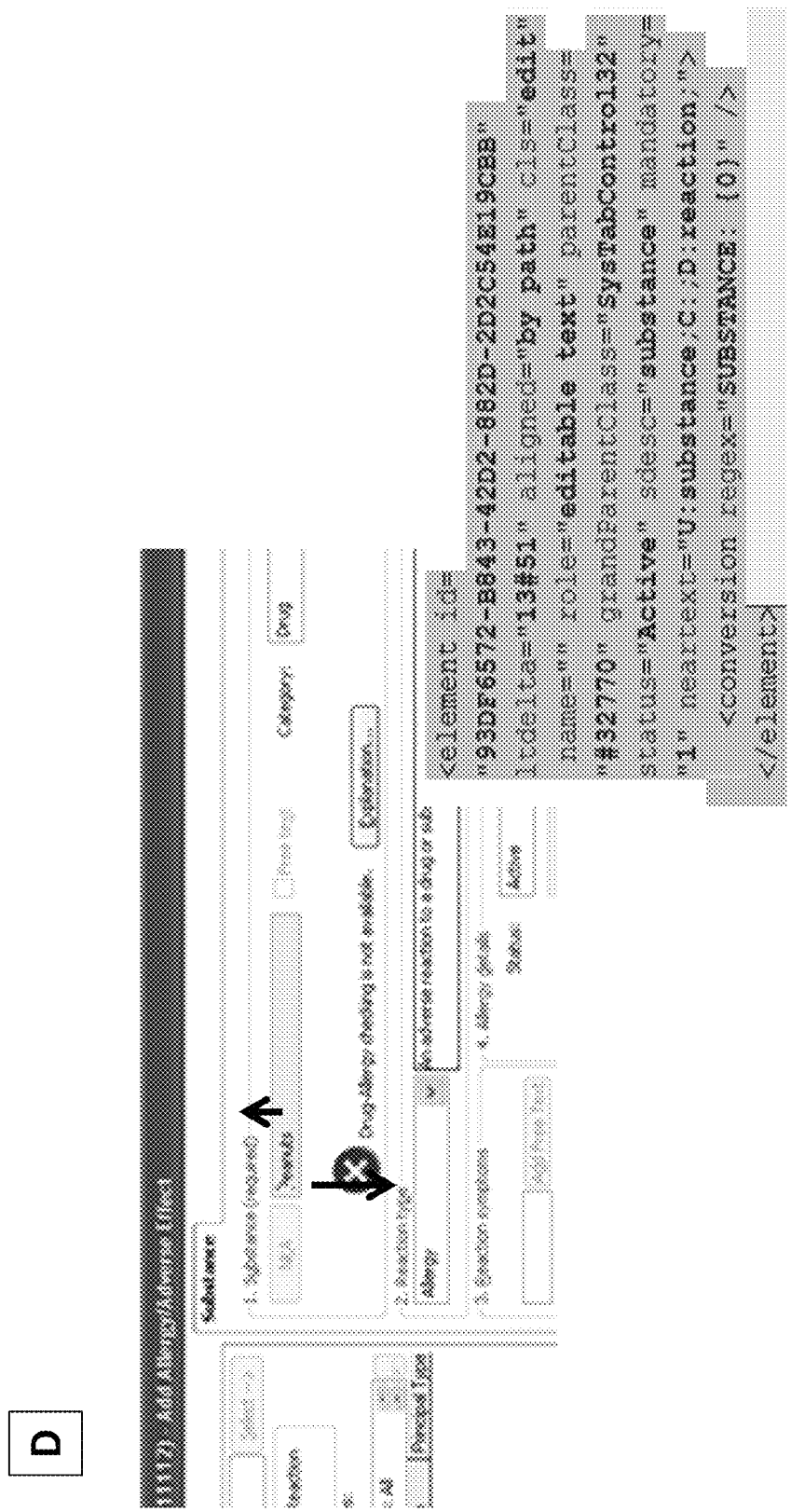

FIG. 18 shows a more complex position matching where the Reader looks for a specific pattern of nearby elements. If a GUI element that matches that pattern, then it can be binded. In the example shown, the Reader looks for an element that when the user looks above it on the screen will see the phrase "substance," and when the user looks below it will see the phrase "Reaction."

Figure 19:
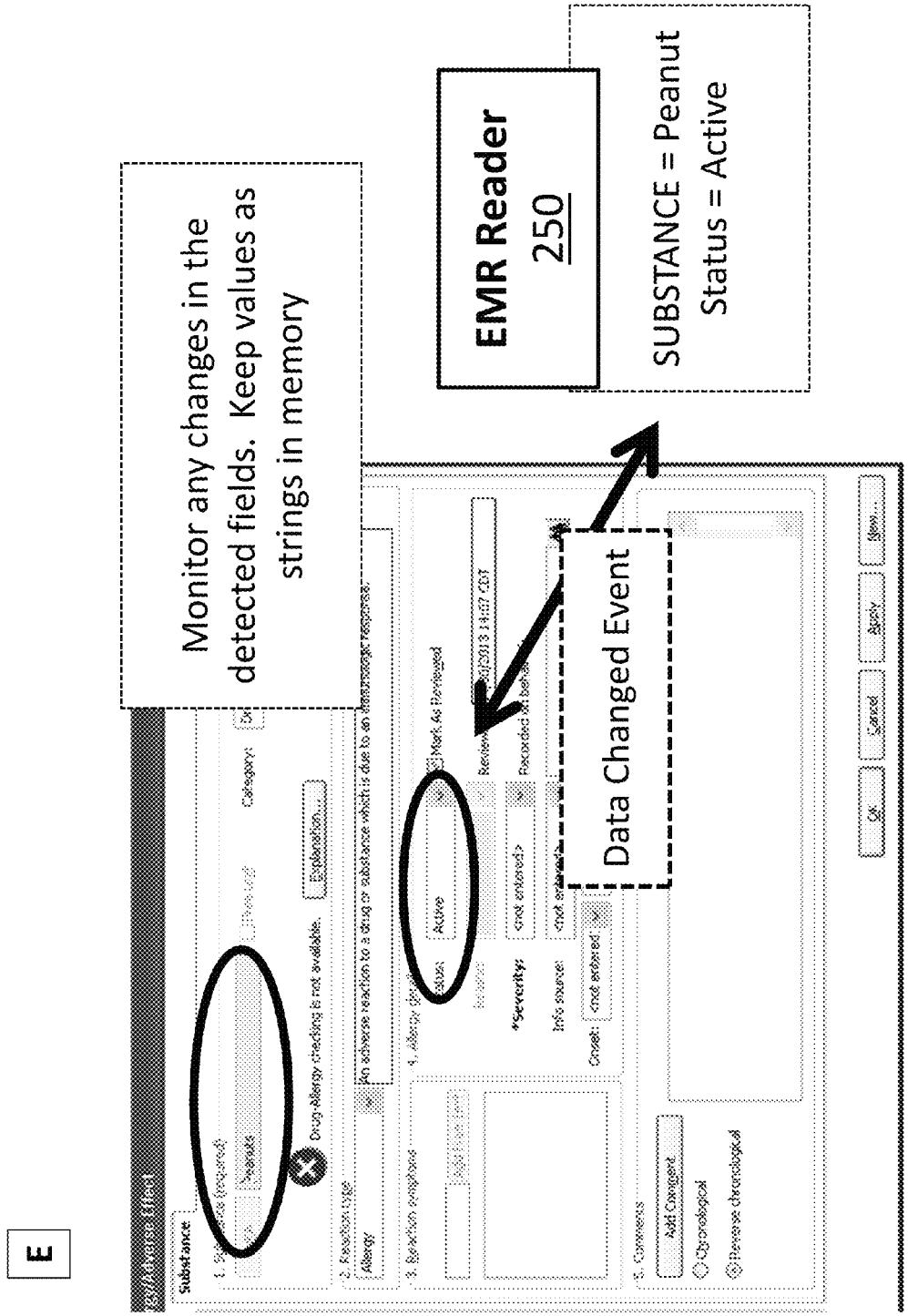

As shown in FIG. 19, the EMR Reader 250 can be configured to monitor any changes in the detected fields (e.g., binded elements). When a change is detected, the EMR Reader 250 triggers a "Data Changed Event" and records the change. In some variations, the change(s) are stored in a temporary memory. In some variations, the change(s) can be stored as strings in memory. In this example, EMR Reader 250 recognizes two changes: that the Substance is Peanut, and the Status is Active.

Figure 20:
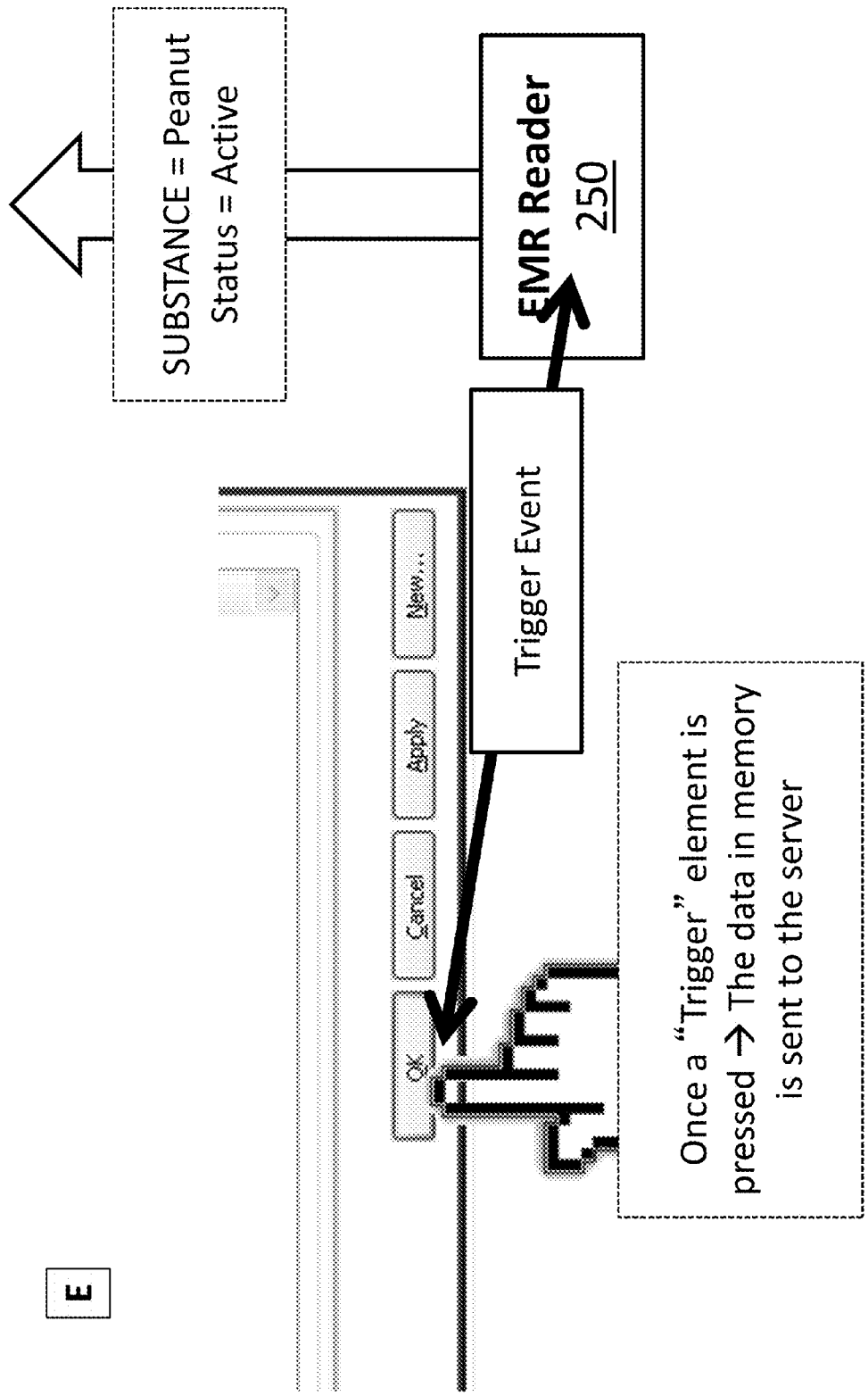

At 650, the EMR Reader attaches the change(s) to a screen, and register identified GUI elements (e.g., including detecting the screen and binding the GUI elements as discussed above). For example, as shown in FIG. 20, when the user clicks on the "OK" button on the screen, this generates a "Trigger Event" which can in turn trigger the EMR Reader Server(s) to (for example) record the change(s) in a more permanent database (e.g., on the EMR Reader Server(s)) and/or analyze the data.

Keeping the data changes temporarily (e.g., at the local machine and committing those changes only when a Trigger Event occurs can be useful in reducing the amount of data transfers and changes at the EMR Reader Server(s). This can make the communication more efficient, and increase the accuracy of the records at the EMR Reader Server(s). In some variations, however, it may be desirable to commit the changes immediately (for example, to capture a screen that does not require any user input).

Figure 21:
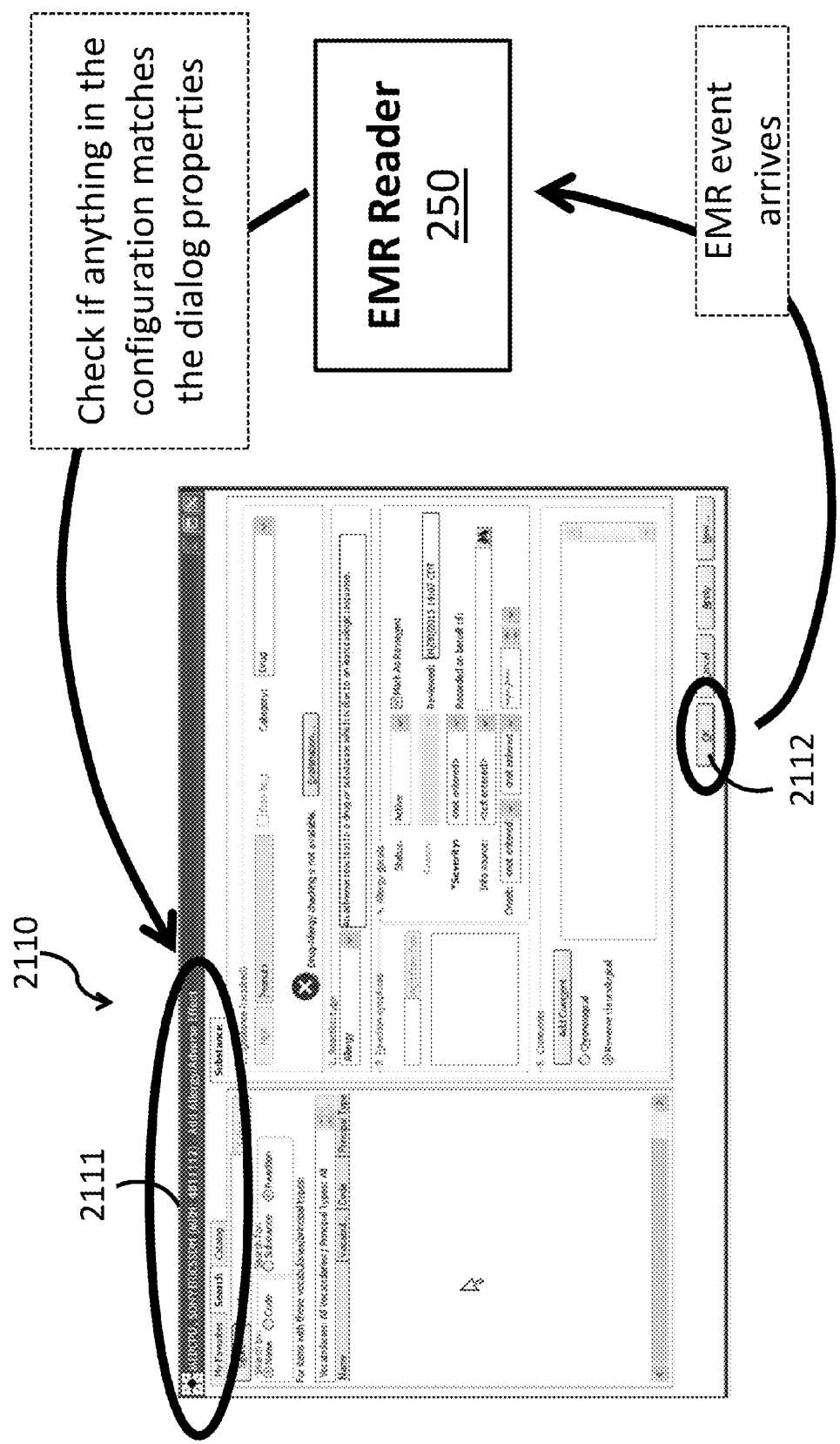

FIG. 21 is a graphical illustration of features of the current subject matter. As shown, when an PAR event arrives (e.g., a "Trigger Event" triggered by clicking the OK button 2112), the EMR Reader 250 can be configured to check if anything in the configuration matches one or more dialog properties. For example, here, the main screen 2110 includes a dialogue 2111 that includes the patient name and a unique ID of the patient. This can be used to match up the patient (which can be particularly important for medical records), and/or to match up the windows on the screen.

Figure 22:
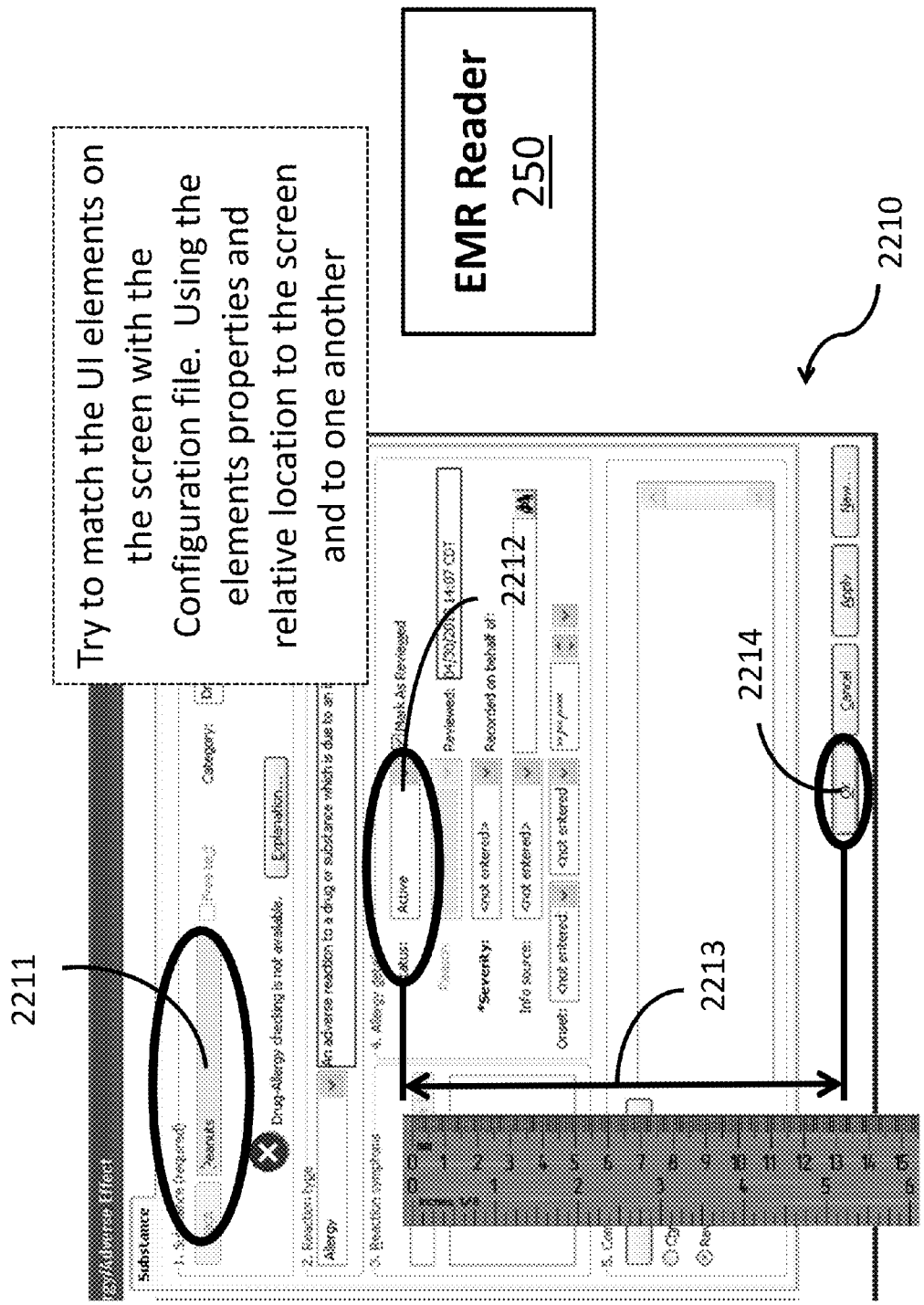

FIG. 22 is another graphical illustration of some of the features of the current subject matter. Here, the EMR Reader 250 tries to match the UI elements (2211, 2212, 2114) of screen 2210 with the Configuration file (for example). In this example, various element properties and relative location (2213) to the screen and to another can be used.

In some variations, the EMR Reader is constantly "listening" to events from the operating system. So, for example, when a new screen is opened in the EMR, an event representing the opening of the new screen is received. Upon this event, one or more foreground windows are sampled, for example, as discussed above.

In some variations, it is important to obtain the patient and/or user context. For example, in the case of EMR, it is important that all the changes will actually be attributed to the right patient (e.g., using a unique ID). Accordingly, the EMR Reader 250 can be configured to extract the patient/user context and make sure that this has not been changed when a new screen/window is opened. In some variations, the patient (e.g., name and/or ID) is presented as a label inside the screen/window and the EMR Reader can obtain it accordingly. In some variation, every screen can be converted to a text message that has the patient's info.

In some variations, optical character recognition (OCR) technology can be employed. For example, in some variations, OCR can be employed to read data from elements already binded (using, for example, one or more features discussed herein). In some variations, OCR the Reader detection features discussed herein are employed and OCR is utilized to detect changes in the data and to capture the data when the changes cannot be captured directly from the electronic data.

Although the current subject matter has been described above with respect to EMR in the medical setting, the current subject matter can be implemented to provide one or more features in other settings. For example, the current subject matter can be used to capture data from an existing sales record system or other record systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the ten "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but Trot limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method comprising:
executing, using at least one data processor, an electronic medical record (EMR) system;
executing, using the at least one data processor, a computer program that is separate from the EMR system to extract data from the EMR system, the execution of the computer program resulting in operations comprising
receiving by the computer program, using the at least one data processor, a screen of a graphical user interface (GUI) of the EMR system comprising a plurality of windows rendering data generated by the EMR system;
determining by the computer program, for each of the windows, whether the window is configured to receive data input from a user, the determination being made using the at least one data processor;
generating by the computer program, for each window configured to receive data input, a list of multiple candidate configuration files that correspond to the window of the EMR system, the generating of the list being based on a size and position of the window;
selecting by the computer program, for each window configured to receive data input, a configuration file from the list that corresponds to the window of the EMR system, wherein the selecting comprises
(i) determining properties of GUI elements of the window,
(ii) selecting a configuration file from the list having a set of configuration elements with properties that correspond to those of the GUI elements of the EMR system, and
(iii) binding GUI elements of the window with corresponding configuration elements of the set of configuration elements, the binding of a GUI element to a corresponding configuration element comprising creating an object in memory that is configured to monitor in real time the GUI element of the EMR system for changes in data, the GUI elements associated with medical data of the patient;
using the objects in memory to monitor in real time the GUI elements of the EMR system that are bound with the corresponding configuration elements for changes in data; and
when one of the objects in memory detects a change in data in a GUI element of a window configured to receive data input in the EMR system, the computer program storing the detected change in real time using the at least one data processor, the stored change being associated with a configuration element of the configuration file that corresponds to the window configured to receive data input.

2. The method according to claim 1, wherein the change is stored temporarily at a local computer terminal where the screen is displayed to the user.

3. The method according to claim 2, further comprising detecting, using at least one data processor, a trigger event, and when the trigger event is detected, storing, using at least one data processor, the change in long-term data storage.

4. The method according to claim 3, wherein the change is stored in long-term data storage only when the trigger event is detected.

5. The method according to claim 1, further comprising listening, using at least one data processor, for a new screen, and determining, using at least one data processor, whether the new screen concerns a same patient as the screen.

6. The method according to claim 1, wherein the screen is implemented in HTML and changes in the screen are monitored by creating objects in memory that correspond to elements in a document object module tree.

7. The method of claim 1, wherein the screen is received by taking a screenshot that is parsed and analyzed using optical character recognition (OCR).

8. The method of claim 1, wherein the plurality of windows is based upon a user configuration that is different from a standard configuration.

9. The method of claim 1, wherein additional data comprising an element position is used in conjunction with the set of configuration elements to perform the selecting.

10. A non-transitory computer readable medium storing instructions, which when executed by at least one data processor of at least one computing system, result in operations comprising:
    executing an electronic medical record (EMR) system;
    executing a computer program that is separate from the EMR system to extract data from the EMR system, the execution of the computer program resulting in steps comprising
        receiving by the computer program, using the at least one data processor, a screen of a graphical user interface of the EMR system comprising a plurality of windows rendering data generated by the EMR system;
        determining by the computer program, for each of the windows, whether the window is configured to receive data input from a user, the determination being made using the at least one data processor;
        generating by the computer program, for each window configured to receive data input, a list of multiple candidate configuration files that correspond to the window of the EMR system, the generating of the list being based on a size and position of the window;
        selecting by the computer program, for each window configured to receive data input, a configuration file from the list that corresponds to the window of the EMR system, wherein the selecting comprises
            (i) determining properties of GUI elements of the window,
            (ii) selecting a configuration file from the list having a set of configuration elements with properties that correspond to those of the GUI elements of the EMR system, and
            (iii) binding GUI elements of the window with corresponding configuration elements of the set of configuration elements, the binding of a GUI element to a corresponding configuration element comprising creating an object in memory that is configured to monitor in real time the GUI element of the EMR system for changes in data, the GUI elements associated with medical data of the patient;
    using the objects in memory to monitor in real time the GUI elements of the EMR system that are bound with the corresponding configuration elements for changes in data; and
    when one of the objects in memory detects a change in data in a GUI element of a window configured to receive data input in the EMR system, the computer program storing the detected change in real time using the at least one data processor, the stored change being associated with a configuration element of the configuration file that corresponds to the window configured to receive data input.

11. The non-transitory computer readable medium according to claim 10, wherein the change is stored temporarily at a local computer terminal where the screen is displayed to the user.

12. The non-transitory computer readable medium according to claim 11, further comprising detecting, using at least one data processor, a trigger event, and when the trigger event is detected, storing, using at least one data processor, the change in long-term data storage.

13. The non-transitory computer readable medium according to claim 12, wherein the change is stored in long-term data storage only when the trigger event is detected.

14. The non-transitory computer readable medium according to claim 10, further comprising listening, using at least one data processor, for a new screen, and determining, using at least one data processor, whether the new screen concerns a same patient as the screen.

15. The non-transitory computer readable medium according to claim 10, wherein the screen is implemented in HTML and changes in the screen are monitored by creating objects in memory that correspond to elements in a document object module tree.

16. A system comprising:
    at least one data processor; and
    memory storing instructions which, when executed by the at least one data processor, result in operations comprising:
    executing an electronic medical record (EMR) system;
    executing a computer program that is separate from the EMR system to extract data from the EMR system, the execution of the computer program resulting in steps including
        receiving by the computer program, using the at least one data processor, a screen of a graphical user interface of the EMR system comprising a plurality of windows rendering data generated by the EMR system;
        determining by the computer program, for each of the windows, whether the window is configured to receive data input from a user, the determination being made using the at least one data processor;
        generating by the computer program, for each window configured to receive data input, a list of multiple candidate configuration files that correspond to the window of the EMR system, the generating of the list being based on a size and position of the window;
        selecting by the computer program, for each window configured to receive data input, a configuration file from the list that corresponds to the window of the EMR system, wherein the selecting comprises (i) determining properties of GUI elements of the window,
(ii) selecting a configuration file from the list having a set of configuration elements with properties that correspond to those of the GUI elements of the EMR system, and
(iii) binding GUI elements of the window with corresponding configuration elements of the set of configuration elements, the binding of a GUI element to a corresponding configuration element comprising creating an object in memory that is configured to monitor in real time the GUI element of the EMR system for changes in data, the GUI elements associated with medical data of the patient;

using the objects in memory to monitor in real time the GUI elements of the EMR system that are bound with the corresponding configuration elements for changes in data; and when one of the objects in memory detects a change in data in a GUI element of a window configured to receive data input in the EMR system, the computer program storing the detected change in real time using the at least one data processor, the stored change being associated with a configuration element of the configuration file that corresponds to the window configured to receive data input.

17. The system according to claim 16, wherein the change is stored temporarily at a local computer terminal where the screen is displayed to the user.

18. The system according to claim 17, wherein the operations further comprises detecting, using at least one data processor, a trigger event, and when the trigger event is detected, storing, using at least one data processor, the change in long term data storage.

19. The system according to claim 18, wherein the change is stored in long-term data storage only when the trigger event is detected.

20. The system according to claim 16, wherein the operations further comprises listening, using at least one data processor, for a new screen, and determining, using at least one data processor, whether the new screen concerns a same patient as the screen.

* * * * *

UNITED STATES PATENT AND TRADEMARK OFFICE
CERTIFICATE OF CORRECTION

| | |
|---|---|
| PATENT NO. | : 9,996,216 B2 |
| APPLICATION NO. | : 14/750724 |
| DATED | : June 12, 2018 |
| INVENTOR(S) | : Noam Velan and Eyal Ephrat |

It is certified that error appears in the above-identified patent and that said Letters Patent is hereby corrected as shown below:

Column 1, Line 12, delete "(ERR)" and replace it with --(EHR)--.

Column 1, Line 23, delete "orders and exam" and replace it with --orders an exam--.

Column 1, Line 26, delete "as in can" and replace it with --as it can--.

Column 1, Line 31, delete "in many EMR" and replace it with --in many EMRs--.

Column 4, Line 56, delete "reused different screens, hut can be" and replace it with --reused in different screens, can be--.

Column 5, Line 64, delete "to be binded" and replace with --to be bound--.

Column 5, Line 66, delete "are binded" and replace with --are bound--.

Column 6, Lines 7-8, delete "are no initially "binded"" and replace with --are not initially "bound"--.

Column 6, Line 20, delete "can be "binded"" and replace with --can be "bound"--.

Column 6, Line 36, delete "that is binded" and replace with --that is bound--.

Column 7, Line 5, delete "will be binded" and replace with --will be bound--.

Column 7, Line 23, delete "be binded" and replace with --be bound--.

Column 9, Line 5, delete "herein, the ten" and replace with --herein, the term--.

Column 9, Line 36, delete "but Trot limited to" and replace it with --but not limited to--.

Signed and Sealed this
Twenty-eighth Day of August, 2018

Andrei Iancu
*Director of the United States Patent and Trademark Office*